US009610335B2

(12) United States Patent
Pereira Da Conceição et al.

(10) Patent No.: US 9,610,335 B2
(45) Date of Patent: Apr. 4, 2017

(54) IMMUNOGENS, COMPOSITIONS AND USES THEREOF, METHOD FOR PREPARING SAME

(75) Inventors: Maria Antónia Pereira Da Conceição, Coimbra (PT); Sofia Judite Marques Da Costa, Santo Tirso (PT); António Manuel Oliveira Castro, Vila Nova de Gaia (PT); André Augusto Da Silva Almeida, Branca (PT)

(73) Assignees: ESCOLA SUPERIOR AGRÁRIA DE COIMBRA, Coimbra (PT); HITAG—BIOTECHNOLOGY, LDA., Branca (PT)

( * ) Notice: Subject to any disclaimer, the term of this patent is extended or adjusted under 35 U.S.C. 154(b) by 0 days.

(21) Appl. No.: 13/514,987

(22) PCT Filed: Dec. 10, 2009

(86) PCT No.: PCT/PT2009/000075

§ 371 (c)(1), (2), (4) Date: Sep. 12, 2012

(87) PCT Pub. No.: WO2011/071404

PCT Pub. Date: Jun. 16, 2011

(65) Prior Publication Data

US 2012/0328621 A1 Dec. 27, 2012

(51) Int. Cl.

| | |
|---|---|
| ***C07K 14/435*** | (2006.01) |
| ***C07K 14/44*** | (2006.01) |
| ***C07K 14/195*** | (2006.01) |
| ***C07K 14/005*** | (2006.01) |
| ***A61K 39/395*** | (2006.01) |
| ***A61P 37/04*** | (2006.01) |
| ***A61K 39/00*** | (2006.01) |

(52) U.S. Cl.
CPC ................................ *A61K 39/0003* (2013.01)

(58) Field of Classification Search
None
See application file for complete search history.

(56) References Cited

U.S. PATENT DOCUMENTS

| | | | | |
|---|---|---|---|---|
| 6,221,619 | B1 * | 4/2001 | Maine et al. | 435/7.22 |
| 7,534,437 | B2 * | 5/2009 | Tendler et al. | 424/185.1 |
| 2004/0033564 | A1 | 2/2004 | Seong et al. | |
| 2007/0021332 | A1 * | 1/2007 | Tendler et al. | 514/12 |

FOREIGN PATENT DOCUMENTS

| | | | |
|---|---|---|---|
| EP | 1 231 217 | A2 | 8/2002 |
| WO | 86/03680 | A1 | 7/1986 |
| WO | 97/01627 | A1 | 1/1997 |
| WO | WO 2004050883 | A2 * | 6/2004 |
| WO | 2008/002166 | A2 | 1/2008 |
| WO | WO 2008002166 | A2 * | 1/2008 |

OTHER PUBLICATIONS

Terpe 2003 (Overview of tag protein fusion: from molecular and biochemical fundamentals to commercial systems; Appl. Microbiol. Biotechnol. 60:523-533).*

Esteban et al. 2002 (High fascioliasis infection in children linked to a man-made irrigation zone in Peru; Tropical and International Health; 7(4) 339-348).*

Greenspan et al. 1999 (Defining epitopes: It's not as easy as it seems; Nature Biotechnology, 17:936-937).*

Honey Reddi et al.; "The Calcium-binding protein of Entamoeba histolytica as a fusion partner for expression of peptides in *Escherichia coli*"; Biotechnology and Applied Biochemistry, Academic Press, US; vol. 36, Aug. 2, 2002; pp. 213-218; XP009131343.

Edward R. Lavallie et al.; "A Thioredoxin Gene Fusion Expression System That Circumvents Inclusion Body Formation in the *E. coli* Cytoplasm"; Bio/Technology, Nature Publishing Co. New York, US; vol. 11, No. 2, Feb. 1993; pp. 187-193; XP000195207.

Athanaslos Theologis et al.; "Sequence and analysis of chromosome 1 of the plant *Arabidopsis thaliana*"; Nature, Nature Publishing Group, London, GB; vol. 408, Dec. 14, 2000; pp. 816-820; XP002953149.

Mary Ann Moran et al.; "Genome sequence of Silicibacter pomeroyi reveals adaptations to the marine environment"; Nature, Nature Publishing Group, London, GB; vol. 432, No. 7019, Dec. 16, 2004; pp. 910-913; XP009090310.

Database UniProt; Feb. 1, 2005; "SubName: Full=Putative uncharacterized protein"; XP002575054.

Chu di Guan et al.; "Vectors that facilitate the expression and purification of foreign peptides in *Escherichia coli* by fusion to maltose-binding protein"; Gene, Elsevier, Amsterdam, NL; vol. 67, No. 1, Jul. 15, 1988; pp. 21-30; XP025705742.

Y. Zhang et al.; "Expression of Eukaryotic Proteins in Soluble Form in*Escherichia coli*"; Protein Expression and Purification, Academic Press, San Diego, CA; vol. 12, No. 2, Mar. 1, 1998; pp. 159-165; XP004447536.

(Continued)

*Primary Examiner* — Gary Nickol
*Assistant Examiner* — Mary Lyons
(74) *Attorney, Agent, or Firm* — Kenealy Vaidya LLP

(57) ABSTRACT

The invention relates to fusion proteins comprising an amino acid sequence of a fragment H corresponding to a fragment of a calcium binding protein excreted-secreted by adult worms of *Fasciola hepatica*, followed by an amino acid sequence corresponding to a unrelated protein or fragment of protein, pharmaceutical compositions, vaccines and adjuvants containing the immunogen, to a process for their preparation, another process for the production of antibodies and their use.

The present invention relates to the preparation of immunogens by the addition of a peptide sequence.

Thus the present invention is useful for producing an immune response, with increases in specific antibody titers in serum against proteins or other antigens and can be applied in particular for the production of specific polyclonal antibodies, immunotherapy and immunoprophylaxis. The addition of the polypeptide to a target antigen, either through the production of recombinant proteins containing the polypeptide or by addition or fusion of this polypeptide with the target antigen, induces a significant increase in the immunogenicity of these molecules, amplifying the immune response elicited by injection of this molecule in a subject susceptible to produce antibodies.

14 Claims, 16 Drawing Sheets

(56) References Cited

OTHER PUBLICATIONS

Database UniProt; May 1, 2000; "SubName: Full=T23K8.7"; XP002575055.
Edward R. Lavallie et al.; "Gene fusion expression systems in *Escherichia coli*"; Current Opinion in Biotechnology, London, GB; vol. 6, No. 5, Jan. 1, 1995; pp. 501-506; XP007912375.
Bowie et al. Deciphering the message in protein sequences: tolerance to amino acid substitutions. Science, 247: 1306-1310, 1990.
Whisstock et al. Prediction of protein function from protein sequence and structure. Quarterly Reviews in Biophysics. 36(3): 307-340, 2003.
Arnau et al. Current strategies for the use of affinity tags and tag removal for the purification of recombination proteins. Protein Expression and Purification. 48: 1-13, 2006.
Lazar et al. Transforming Growth Factor alpha: Mutation of Aspartic Acid 47 and Leucine 48 Results in Different Biological Activities. Molecular and Cellular Biology, 8(3): 1247-1252, 1988.
Laura Cervi et al.; "Involvement of excretion-secretion products from Fasciola hepatica inducing suppression of the cellular immune responses"; Veterinary Parasitiology 61; 1996, 97-111.
Silva, M.L. et al.; "Putative calcium-binding protein [Fasciola hepatica]"; NCBI GeneBank AA F31420.1 (Feb. 7, 2000) http://www.ncbi.nlm.nih.gov/protein/AAF31420.1.
Database UniProt; Feb. 1, 2005; "SubName: Full=Putative uncharacterized protein"; XP002589968.
Silva Elisabete et al.; "A Recombinant Antigen Recognized by Fasciola Hepatica-Infected Hosts"; The Journal of Parasitology; American Society of Parasitologists, US LNKD-DOI:10.1645/GE-136R; vol. 90, No. 4, Aug. 1, 2004; pp. 746-751; XP008087125.
International Search Report for PCT/PT2009/000075 Jul. 16, 2010.

* cited by examiner

```
Fh8      MP SVQEVE KLLHVLDRNGDGKVS
Frag H   MP SVQEVE KLL

Fh8     AEEL KAFADDSKCPLDSNK I KA F

Fh8     IKEHDKNKDGKLDLKELVS I L S S
```

Figure 1

C
a) b)
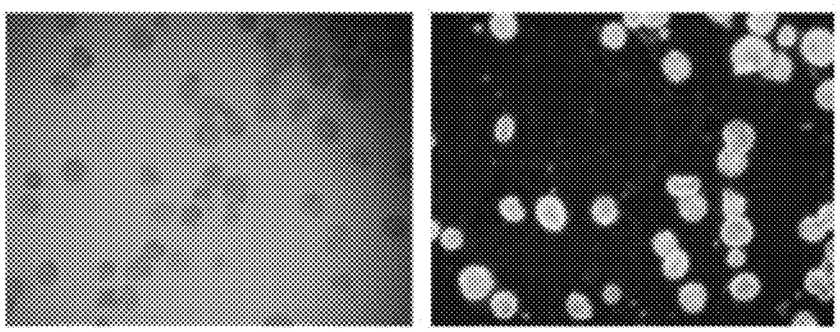
Figure 6 - C

IMMUNOGENS, COMPOSITIONS AND USES THEREOF, METHOD FOR PREPARING SAME

CROSS REFERENCE TO RELATED APPLICATIONS

This application is a U.S. national phase filing under 35 U.S.C. §371 of PCT Application No. PCT/PT2009/000075, filed Dec. 10, 2009

INCORPORATION-BY-REFERENCE OF MATERIAL SUBMITTED ON A COMPACT DISC

The instant application contains a Sequence Listing that has been submitted in ASCII and PDF format via EFS-Web and is hereby incorporated by reference in its entirety. Said ASCII copy, created on Jun. 6, 2012 is named Seq_List_as-filed_PTI_US45659-12 and is 13 kb in size.

BACKGROUND

Field

The present invention relates to the preparation of immunogens, a process for their preparation and their use in expression systems for the production of recombinant proteins.

The present invention describes a sequence that added by conjugating, either by chemical or physical methods, to an unrelated antigen, or through incorporation into a recombinant antigen or in the plasmid DNA strand containing the unrelated sequence for the antigen with the purpose of developing an immune response against the unrelated antigen.

The present invention describes a novel adjuvant whose application can lead to production of immunogens (including recombinant proteins containing the peptide sequence) that induce an immune response characterized by the production of specific antibodies. In this application the not related fragment develops (for poorly immunogenic antigens) immunological characteristics that leads to the development, simply by his administration to the host, of a immunological response by the host, characterized in particular by the production of specific immunoglobulins.

The antisera are usually produced by the injection of an immunogen of interest in an animal, often in combination with an adjuvant to increase the immune response. The answer may be increased by subsequent administrations of the antigen, with or without adjuvant. The amount of immunogen to be administered to produce the desired response varies greatly depending on the species and/or subspecies of animal used, the adjuvant used, the route of administration, frequency of injections, and immunogenicity of self antigens. The quality and quantity of antibodies obtained depend on the size and condition of the immunogen. Small polypeptides and non-protein molecules may require a combination of larger proteins in order to originate an immune response.

One area of application of adjuvant-type substances will be vaccinology. In general, several hundred natural and synthetic compounds were identified as having adjuvant activity. It appears that the toxicity of these is the main obstacle to its use, including at human level. Most side effects occurring in the production of polyclonal antibodies, both in severity and duration, results from the presence of adjuvant.

The adjuvants can be used with different purposes, including: enhancing the immunogenicity of a purified or recombinant, reduce the amount of antigen or the number of immunizations required to induce protective immunity, and improving the effectiveness of the vaccine in newborns, the elderly or individuals with a immunological compromised system; as delivery system of the antigen or antigen uptake through the mucosa. The benefits of incorporating the adjuvant in any formulation have to be balanced with the risk of adverse reactions. One of the biggest challenges in search of an adjuvant is to increase power and minimize toxicity.

Due to the effects of size, electric charge and hydrophobicity, which regulate the incorporation of proteins in the formulation of the adjuvant, it is difficult to predict what will be the most effective adjuvant for a particular protein or peptide. Besides, changes in the epitopes may occur during the formulation or combination. In the case of transport proteins the existence of immunity towards that protein is a major limitation. Furthermore, each adjuvant generates a characteristic immune response.

The increasing use of vaccines composed of recombinant subunits and has made the need to improve the processing a priority.

SUMMARY

The aim of the present invention is to describe a process of producing immunogens resulting from the addition of the peptide with the sequence: MPSVQEVEKLL (SEQ ID NO 2) called H fragment, derived from a calcium binding protein of *Fasciola hepatica*, to an unrelated antigen. The resulting construction has immunogenic characteristics triggering an immune response when administered to an individual, characterized by the production of specific antibodies against the unrelated antigen.

The present invention is useful for any application with the aim of producing an immune response against an antigen by an individual, by the administration of an immunogen consisting of the fragment H and the unrelated antigen. The present invention describes an application of a new adjuvant that may be applied, both at research and development or industrial levels, in areas such as production of polyclonal and monoclonal antibodies, immunotherapy and immunoprophylaxis.

The present invention represents an alternative to current adjuvants and, when used in systems for expression of recombinant antigens allows the production of proteins with immunogenic characteristics that, without any other additive, leads to the development of an immune response in an individual that is able to develop an immune response. Currently, one of the greatest challenges in the development of antibodies is to obtain a sufficiently immunogenic antigen to develop the immune response. When the antigen is not or poorly immunogenic, the administration of the antigen with adjuvants is used to enhance the immune response. These adjuvants are potentially toxic, may cause pain in the injected host and therefore its use is highly discouraged, or in many adjuvants is even prohibited. The advantage of the current applications resides in this point in the state of the art, since it describes a methodology that allows the obtaining of modified antigens with immunogenic characteristics to develop an immune response without the use of adjuvants.

One of the achievements of the present invention is the description of an immunogen comprised of:

part of the sequence of amino acids from a calcium binding protein excreted/secreted by adult worms of *Fasciola hepatica* with the sequence identical or at least 90% structurally similar to SEQ ID NO 2. designated by fragment H;

a not related protein or protein fragment of interest.

Another preferential implementation of the present invention is that the protein or protein fragment of interest to be a pathogenic protein such as a viral protein, a bacterial protein or a protein from a protozoan. Even more preferably, the protein or protein fragment of interest may be the CWG, CD4, the IL5, the Pfsp, the Ent, the PAL, the CP12, the LEC, the BG or the Toxo proteins or proteic fragments.

In a further preferential realization the immunogens described above may be used as medicines. Even more preferentially may be used as vaccines or adjuvants. We note that in some cases even more preferential, may be used a vaccine that comprises only:

part of the sequence of amino acids from a calcium binding protein excreted/secreted by adult worms of *Fasciola hepatica* with the sequence identical or at least 90% structurally similar to SEQ ID NO 2. designated by fragment H;

a not related protein or protein fragment of interest.

Another preferential achievement is the description of compositions containing the immunogens described above, and preferably the compositions may contain the immunogens in therapeutically effective amounts and with a pharmacologically suitable vehicle, such as excipients, adjuvants, among others.

In another preferential implementation, the compositions may contain only 100% of one of the immunogens described above.

In carrying out even more preferentially the compositions may be constituted by the following elements: by an immunogens described above with concentration between 1 to 100 μg diluted in a volume between 100 to 1000 μl of buffered phosphate solution (0.01M phosphate, 0.1 M NaCl, pH 7.2).

Another achievement of the present invention is the description of an adjuvant comprising one of the immunogens described above or one of the pharmaceutical compositions described above.

We used an adjuvant containing: the fragment H added to the fragments CWG and CP12 between 1 and 100 μg diluted in a volume between 100 and 1000, μl of phosphate buffer—0.01 M phosphate, 0.1 M NaCl, pH 7.2 administered to mice, this administration induced an increase in the intensity and the speed with which it developed an immune response against specific fragments CWG and CP12.

Still another embodiment of the present invention is the description of a vaccine that includes one of the immunogens described above or one of the pharmaceutical compositions described above. We used an adjuvant containing: the fragment H added to the fragments CWG, BG and CP12 between 1 and 100 μg diluted in a volume between 100 and 1000, μl of phosphate buffer—0.01 M phosphate, 0.1 M NaCl, pH 7.2 administered to mice, the administration of this vaccine reduced the intensity of infection found in experimental infection by *Cryptosporidium* and *Giardia*.

In yet another preferential implementation, we developed a method for the preparation of immunogens described above which comprises the addition of a fragment H polypeptide not related in any position in the sequence corresponding to the polypeptide of interest, the addition of fragment H at the start, end or at location of the polypeptide of interest. Even more preferentiality can be used to several proteic fragments and/or proteins such as the CWG, CD4, IL5, Pfsp, Ent, PAL, CP12, LEC, BG or Toxo.

In yet another embodiment most preferential, describes a method for the production of polyclonal antibodies, isolated and purified, or a functional fragment that is capable of recognizing an immunogen as described above or obtained by the method described above, where the method for obtain antibodies comprises the following steps: immunization of a non-human mammal subject with any of the immunogens described above or with one of the compositions described above; selection of antibodies that are able to recognize the immunogen described above or obtained by the method of preparation of immunogens using methods described for this purpose. For example, the use of columns of CNBr-Sepharose coupled with the immunogen in which, by affinity chromatography, the antibodies that recognize the immunogen are isolated.

Thus the present invention is useful for producing an immune response, with increases in specific antibody levels in serum against proteins or other antigens and can be applied, in particular, for the production of polyclonal specific antibodies, immunotherapy and immunoprophylaxis, in the production of vaccines, adjuvants, diagnostics methods and other applications directly obtained through the development of a specific immune response.

The addition of the polypeptide target to the H fragment SEQ ID NO. 2, either through the production of recombinant proteins containing the polypeptide or by addition or fusion of this polypeptide with the target antigen, induces a significant increase in the immunogenicity of these molecules, allowing to amplify the immune response elicited by injection of this molecule in a in a subject susceptible to produce antibodies.

BRIEF DESCRIPTION OF FIGURES

Figure 1:
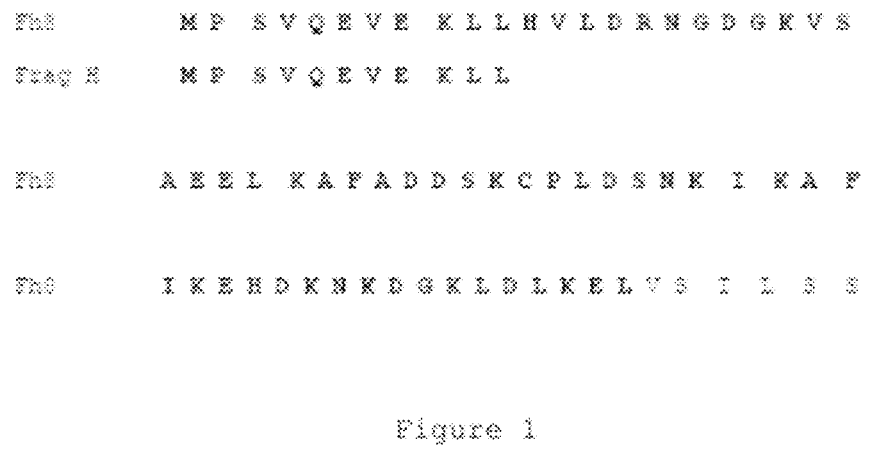

FIG. 1—Characterization of the calcium binding protein FH8 and of the peptide fragment H. Fh8—The deduced amino acid sequence for the FH8 polypeptide (SEQ ID NO 1), Frag H-deduced amino acid sequence for the polypeptide referred to as fragment H (SEQ ID NO 2).

GENERAL DESCRIPTION OF DISCLOSED SUBJECT MATTER

Figure 2:
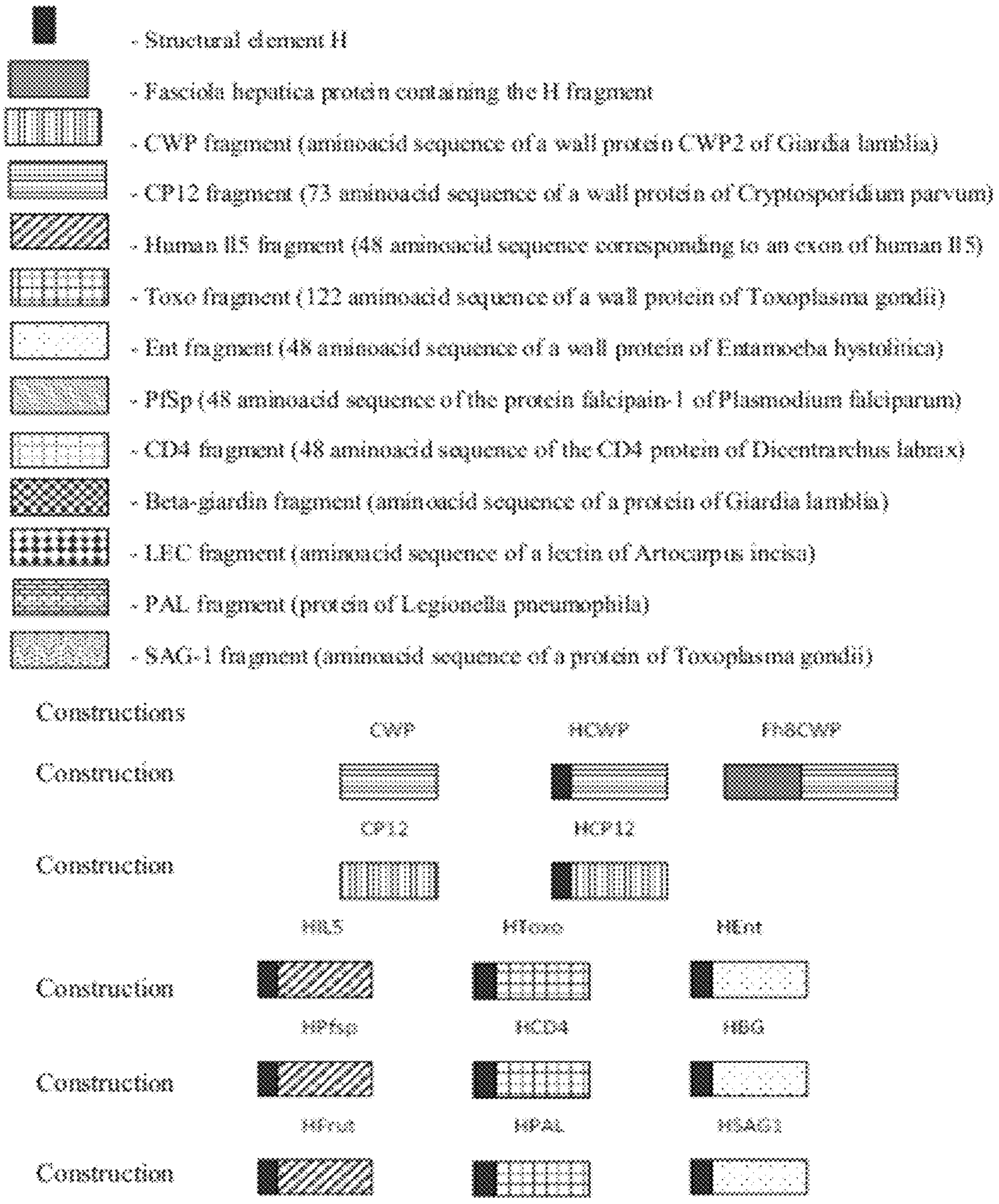
FIG. 2—Schematic of subclonings used to evaluate the effect of fragment H in the induction of immune response.

The present invention relates to fused proteins that comprise the structure: (1) part of the sequence of amino acid from a calcium binding proteins, excreted/secreted by adult worms of *Fasciola hepatica*, and a unrelated protein or protein fragment of interest.

It is also the subject of the present invention a process for the preparation of these fused proteins that allow a dramatic increase of the immune response of animals against the unrelated protein fragment.

The addition of small pieces of calcium binding proteins from the helminth *Fasciola hepatica*—hereafter designated as fragments H—(SEQ ID NO 2) or similar sequences, preferably at least with 90 to 95% homology, preferably with 90%, 91%, 92%, 93%, 94%, 95%, 96%, 97%, 98%, 99% or 100% of similarity, to not related protein fragments or proteins leads to a significant increase in the levels of immunogenicity of polypeptides.

A first aspect of the present invention relates to a fused protein comprising an amino acid sequence with the structure of fragment H, followed by an amino acid sequence structurally similar to a unrelated protein fragment or protein.

Another aspect of the invention relates to an expression vector characterized by comprising a polynucleotide sequence that encodes such fused protein. Yet another aspect of the invention relates to the preparation of the antigen for injection into an animal capable of developing an immune response. The present invention relates also to a process of administration of recombinant antigens to animals that may develop an immune response.

The invention also refers to the use of this fusion protein for the production of polyclonal antibodies specific to the added proteins or protein fragments. The production of these fused proteins can dramatically increase the immunogenicity of the fragments or proteins added, thereby enhancing its use both for research and development for industrial purposes.

The induction of specific immune response against an antigen is a complex process involving a wide variety of cells and mechanisms, often with conflicting activities. The development of methodologies that may lead to the production of an antigen able to induce a more intense immune response, due to potential applications in both R & D as well at the industrial level, in areas as important as the development of vaccines, diagnostics, immunotherapies, etc. . . . has been a constant theme in evolution. Although several substances, such as adjuvants, are known to significantly increase the immune response produced against a target antigen, many of them have side effects that limit their use. On the other hand an application that allows the endogenous increase of immunogenicity of a target antigen has not yet been developed.

We describe an invention that has, as main characteristic, to allow the increase in the immunogenicity of the target molecule, upon the addition of a peptide sequence (fragment H). We describe as examples the application of this invention in the production of recombinant proteins in which the target antigen is produced with this tag. This construction allowed the significant increase in the immunogenicity of the target antigen.

The present invention relates to antigens fused with amino acid sequences present in calcium binding proteins excreted-secreted by adult worms of *Fasciola hepatica*, in particular protein called FH8 or fasciolin (Genbank number AF213970). This strategy can increase the levels of immunogenicity of antigens that are fused to the fragments H, and this increased immunogenicity leads to a gain in the induction of an immune response by individuals to whom it is administered. This system can increase significantly the levels of immunogenicity of the antigen of interest allowing development by the individual to whom it is administered of a more intense immune response, including the production of specific antibodies against the antigen of interest. This process enables the use of low immunogenic antigens, including peptides, in the production of polyclonal antibodies, vaccination, immunotherapy or other applications that may result from the development of a specific immune response.

The immunologic characteristics of the antigen resulting from the addition of the H fragment with the antigen of interest allow the development of a specific response against the antigen of interest without the presence of a significant response against fragment H. The immune response occurs after injection of the immunogen without other additives, including the presence of another adjuvant, the antigen can be administered denatured or not. The results in support of this invention refer to demonstrations using the amino-terminal fragment of 11 amino acids of the protein FH8 to increase the immunogenicity of unrelated proteins or protein fragments that are used as an example. These procedures can be, however, potentially extended to any polypeptide. The demonstrations described are based on the production of recombinant proteins containing the N-terminal sequence corresponding to fragment H. This model of application potentiates the use of this invention because it is no longer required the combination of the peptide by chemical or physical methods. This application also enhances the use of recombinant antigens production systems to produce recombinant immunogens in particular for use in the production of polyclonal antibodies and preparation of vaccines.

DETAILED DESCRIPTION

The statements described to validate the application are based on the use of vector pQE (sourced from Qiagen), commonly used for research purposes. The various constructs were subcloned into the expression vector in *Escherichia coli* pQE (sourced from Qiagen), which results in the production of recombinant proteins expressed in the following N-terminal sequence of 6 histidines, this production performed in *E. coli* M15 (pREP4) (sourced from Qiagen), allowing its isolation by affinity chromatography with a column of NINTA agarose (sourced from Qiagen), based on protocols provided by the manufacturer (Castro, 2001, Silva and al., 2004). All products were made using this system, and we performed the isolation of the recombinant antigen under denaturing conditions to allow more effective isolation.

For the production and isolation of the protein of interest it is possible to use any expression system and isolation of recombinant protein, provided that it does not compromise the exposure of the fragment H on to the immune system. The system used to obtain the constructions should be seen as the vehicle used in research to obtain high quantities of protein needed for experimental demonstrations.

The same methodology can be used in other systems of protein production, in particular fungi or eukaryotic systems.

The results refer to the examples using the fragment H from FH8 (SEQ ID NO 1 and 2).

One of the principles of the invention is characterized by the addition of the fragments H, corresponding to the sequence of the N-terminal fragment of FH8, specifically the addition of the polypeptide SEQ ID NO 2, by processes of molecular biology, before the polypeptide sequence intended to use as immunogen. This constructions can be accomplished by inclusion of this sequence by molecular biology techniques, including using appropriate restriction enzymes to add these fragment in appropriate restriction sites, methodology used in the described demonstrations, or by other processes such as adding DNA fragments with the sequence of interest (linkers) to a PCR product, or other approaches. The reduced amplitude of the fragment H allows the use of a variety of strategies for the merger with the polypeptide of interest.

Another possibility for the construction is the preparation of a fused protein using the polypeptide corresponding to the sequence of the polypeptide FH8 to be manufactured. The process of inserting the following FH8 can be accomplished using the techniques of molecular biology, including the use of restriction enzymes, a methodology used in the process of demonstration.

The invention has been applied to various fragments and proteins with different immunogenic characteristics, including proteins or fragments described as non or poorly immunogenic as CWG, CD4, or fragments that, due to their characteristics, including its molecular weight would be less immunogenic, such as IL5, Pfsp and Ent, proteins described as being very immunogenic as PAL, and proteins and proteic fragments moderately immunogenic, such as CP12 and LEC, as well as other targets with unknown characteristics such as BG and Toxo. We also applied throughout the experiments several different protocols varying in protein concentration of administrations given to mice and the time periods between them. These various protocols were used to demonstrate the versatility of the invention. We also evaluated the possibility of administering the antigen under denaturing conditions, as in the case of the LEC or in non-denaturing, as the case of the remaining fragments and proteins. For all the demonstrations performed we used mice as experimental models and performed the administration of antigens via intra peritoneal. The production of antibodies to targets CWP, IL5, Ent, Toxo, BG and CP12 was also evaluated in rabbits using subcutaneous administration with similar results (not shown). The antigens were produced and isolated under denaturing conditions using the same conditions with NINTA agarose resin (sourced from Qiagen). The antigens were prepared for immunization after dialysis against PBS and sterilization by filtration through a 0.22μ filter.

To demonstrate the specific effect exerted by the fragment at the level of immunogenicity we used two targets, namely:

CWG: CWP (Cyst wall protein) protein of *Giardia lamblia* cysts. On completion of the work we used a part of the sequence of CWP2 of 427 bp, the original sequence has 1089 bp and the region to be amplified is located 527 bp to 931 bp (GenBank access No. XM_001710190). The fragment was amplified by PCR and subcloned into the vector pQE (CWP) were also prepared constructs containing the fragment H followed by the CWP (HCWP) and containing the sequence of FH8 fused with the sequence of the CWP (Fh8CWP). Inocula were administered with the same amount of protein (50 μg) at intervals described in Table 2. The results showed the production of significant levels of anti-CWP only in group HCWP visible after the 5 IP whose presence was maintained throughout the remainder of the experiment, including 83 days after the last administration of protein. The blottings made using the antigen Fh8CWG confirm the results of ELISAs and demonstrate the specificity of antibodies produced. The immunofluorescence assay with the parasite showed that the antibodies produced recognize the native protein that exists in the wall of this structure.

CP12: The CP12 is a surface protein of *Cryptosporidium parvum*. The fragment CP12 (GenBank No. XM_625821) used in this work has 213 bp and corresponds to the nucleotide sequence of the protein CP12 without its transmembrane domain. The fragment was amplified by PCR and subcloned into the vector pQE (CP12,) we also prepared constructs containing the fragment H followed by CP12 (HCP12). The antigens were produced and isolated under denaturing conditions using the same conditions with NINTA agarose resin (sourced from Qiagen). Inocula were administered with the same amount of protein (20 μg) with the periodicity showed in Table 2. The results showed a significant increase in production of antibodies between the CP12 and HCP12 groups, both in intensity and speed, these levels remained significantly increased throughout the experiment. The blottings made with Fh8CP12 confirm the results of ELISAs and demonstrate the specificity of antibodies produced. The immunofluorescence assay with the parasite showed that the antibodies produced recognize the native protein exists in the wall of this structure.

For the remaining targets have prepared groups immunized with the construction containing the H tag to demonstrate the presence of an immune response. For the examples described below, fragments were amplified by PCR with the exception of fragment LEC that was provided by other institutions, and subcloned in the pQE vector containing the fragment H followed by the target fragment. The conditions for obtaining such fragments are described in Table 1.

BG: We cloned the complete sequence of the gene of β-Giardina of *Giardia lamblia* which has a size of 850 bp, with a deletion (691 bp to 787 bp) (GenBank access No. X85985), encoding a protein of 33 kDa. We administered inoculations with the same amount of protein (20 μg) with the periodicity shown in Table 2. The results showed a significant increase after the 3rd IP leveling after the 4th IP. The blottings made with protein BG confirm the specificity of antibodies produced. The maintenance of antibody titers was detected even 47 days after the last inoculation made. immunofluorescence tests with the parasite showed that the antibodies produced recognize the native protein existing in the wall of this structure.

Ent: The amplicon at work has a size of 163 bp encoding a protein with 5 kDa and is the region between 291 bp-453 bp of a gene with a size of 456 bp (No access GenBank XM_645825) from *Entamoeba histolytica* cyst wall specific glicoprotein Jacob. Inocula were administered with the same amount of protein (50 μg) with the periodicity shown in Table 2. The results showed a significant increase after the 4th IP. The blottings made with protein Fh8Ent confirm the specificity of the antibodies produced. We were able to confirm the maintenance of antibody titers even 90 days after the last inoculation made. The immunofluorescence assay with the parasite showed that the antibodies produced recognize the native protein exists in the wall of this structure.

Pfsp: In this study we used a small part of the sequence (165 bp) of falcipaina-1, which is inserted into the sequence of 3D7 *Plasmodium falciparum* trophozoite cysteine proteinase precursor (1423 bp-1587 bp) (N° access GenBank XM_001348691 0.1). Inocula were administered with 50 μg with the periodicity shown in Table 2. The results showed a significant increase after the 4th IP reaching the maximal title after the 7 th IP. We can confirm the presence of specific antibodies against the fragment Pfsp 82 days after the last inoculation. The blottings made with protein Fh8Pfsp confirm the specificity of antibodies produced.

IL5: The human interleukin 5 is a hematopoietic growth factor, having a nucleotide sequence of 816 bp coding for 134 amino acids (GenBank No. BC069137.1). The fragment used for evaluation IL5 is a very small part of IL5, consisting of 144 bp corresponding to an exon of the 5' end of IL5 coding for 48 amino acids. Inocula were administered with the same amount of protein (20 μg) with the periodicity shown in Table 2. The results showed a significant increase after the 4th IP. The blottings made with protein Fh8IL5 confirm the specificity of antibodies produced.

Toxo—Toxo protein is a protein of the oocyst wall of *Toxoplasma gondii* with 1846 bp coding for 499 amino acids (GenBank No. EU851867.1). The Toxo fragment corresponds to exon 2, between the 2875 and 3238 bp. Inocula were administered with the same amount of protein (20 μg) with the periodicity shown in Table 2. The results showed a significant increase after the 4th IP. The blottings made with protein Toxo confirm the specificity of antibodies produced.

CD4: The CD4 protein is a recipient of the wall of lymphocytes of *Dicentrarchus labrax* (GenBank No. AMB849812.1). The CD4 fragment corresponds to two domains of this receptor between 193 and 714 bp. Inocula were administered containing 30 μg with the periodicity shown in Table 2. The results showed a significant increase after the 4th IP. The blottings made with the CD4 protein confirm the specificity of antibodies produced.

PAL: PAL protein (Peptidoglycan-associated lipoprotein precursor) of *Legionella pneumophila* is a protein from the wall of this bacterium (GenBank No. YP001250824). PAL corresponds to the complete protein. We administered an inoculum with 30 μg with the periodicity shown in Table 2. The results showed a significant increase after the 2nd IP. The blottings made with protein PAL confirm the specificity of antibodies produced.

LEC: The DNA fragment of the lectin from *Artocarpus incisa* with 846 bp was containing the local for the enzymes Sac I and KpnI. Since this antigen is potential hemagglutinating activity when in a non-denaturing form, we proceeded with the preparation of protein inocula under denaturing conditions. To remove the maximum amount of urea (final concentration less than 10 mM) we proceeded with the dialysis against PBS buffer with 50 mM urea and at the time of preparation of sample we diluted the antigen in PBS and filtered through 0, 22μ. We administered with an inoculum of 12.5 μg with the periodicity shown in Table 2. The results showed a significant increase after the 4th IP. The blottings made with protein HLEC confirm the specificity of antibodies produced.

In the examples described above evaluation of the response was performed by ELISA using the corresponding antigen. In blotting procedures we evaluate the response to the antigen whose production was more efficient. For blotting performed with recombinant proteins containing the tag FH8, due to the possibility of forming polymers, we proceeded to the location of the recombinant protein with polyclonal antibody specific for FH8. In most cases we included in the blot a nitrocellulose strip containing an antigen with the fragment H, usually the recombinant FH8, for evaluation of the response against this fragment and, apart from the response obtained in the group inoculated with Fh8CWP, we didn't detected the presence of significant levels of antibodies anti-H.

In the examples above the inoculations were always made only by the antigen diluted in PBS, with the exception of HLEC whose inocula consistained 10 mM urea in PBS.

Characterization of Antigen and its Fragment FH8 H:

The antigen FH8 was previously isolated and characterized by elements in the list of inventors (Castro, 2001, Silva et al., 2004, Eguino et al., 1999) (FIG. 1).

The isolation of Fh8 was carried out from the screening of a *F. Hepatica* cDNA bank (FIG. 1). The clones coded for a polypeptide of 69 amino acids with a calculated molecular mass of 8 kDa, which was designated by FH8 or fasciolina (Genbank number AF213970).

The recombinant protein FH8 is produced at high levels of protein in *E. coli* expression systems with vector pQE (>5 mg/liter of culture). Studies with FH8 mutants led to hypothesize that the N-terminal sequence of this antigen have an important role in protein stability. Demonstration of this hypothesis originated the invention described in Patent No. 20091000005031. Another characteristic was its high immunogenicity, this feature extends to another family of calcium binding proteins, present in the extract excreted secreted by adult worms of *Fasciola hepatica*, the family of FH22 (EMBL number AJ003821, EMBL number AJ003822). Both antigens proved to be capable of inducing an immune response with high specific antibody titers (Castro, 2001, Silva et al., 2004). These results also suggested its use as a tag for recombinant protein production with the aim of producing antibodies. The demonstration that the fragment H was essential to the stability of the antigen and that the addition of this fragment to other unrelated proteins or fragments allowed an increase in protein production, presumably due to increased stability of the fused protein, suggested the hypothesis that the addition of fragment H, for the same reasons, would increase the immunogenicity of that antigen. This inference appears from the fact that the stability of a protein is oftenly related to its immunogenicity. This hypothesis was confirmed by the demonstrations described above Strains Used In this study, we used strains *Escherichia coli* XL1 Blue (Stratagene) and *Escherichia coli* M15 [pREP4] (sourced from Qiagen) for the cloning of the plasmids pGEM-T Easy (Promega) and plasmid pQE30 (sourced from Qiagen), respectively.

For protein expression we used the *Escherichia coli* strain M15 [pREP4].

The plasmid DNA was isolated and purified by Kit Wizard® Plus SV Minipreps DNA Purification System from Promega, from bacterial cultures grown at 37° C. overnight, following the instructions provided by the manufacturer.

Constructs

The layout of the buildings used to evaluate the structural element of 11 amino acids (fragment H) as a factor in the induction of immunogenicity of recombinant proteins is shown in FIG. 2.

The constructs shown in FIG. 2 were obtained by polymerase chain reaction (PCR) and cloned into pGEM and then into pQE are shown in Table 1, as indicated below. The constructs referred to other antigens used to evaluate the immune response were obtained by polymerase chain reaction (PCR) and cloned into pGEM and then into pQE are shown in Table 1.

The remaining buildings were obtained by subcloning techniques described below

PCR

The primers used in PCR are described in Table 1.

To obtain the fragments H and Fh8RSac, containing the restriction sites BamHI and SacI, we used as template for the PCR reaction, the pQE30 vector containing the gene coding for the polypeptide FH8 (Castro, 2001, Silva et al., 2004). The PCR reaction began with a denaturation step of 1 minute at 95° C., followed by 30 amplification cycles, with 45 seconds denaturation at 94° C., 30 seconds of annealing at 50° C. and 45 seconds of polymerization at 72° C. We made a step further polymerization for 11 minutes at 72° C.

The fragments chosen (CWG, CP12, BG, Ent, PFSP, IL5, Toxo, CD4, PAL and LEC) to assess the ability of recombinant proteins prepared by the merge of unrelated polypeptides with the H fragment, to produce an immune response, as measured the appearance of specific antibodies against the protein or fragment in question, were amplified by PCR. This PCR reaction also added to the restriction enzymes SacI and KpnI to their fragments.

TABLE 1

List of PCR reactions performed to obtain constructs used to evaluate the fragment H activity, DNA samples, primers and PCR program

| Purpose | DNA sample used as template | primers used | PCR program |
|---|---|---|---|
| Obtaining of fragment H | Plasmid DNA-vector pQE30 containing the sequence of DNA coding for Fh8 | HBamSac:<br>5'-G A T C C A T G C C T A G T G T T C A A G A G G T T G A A A A A C T C C T T G A G C T C C A G T-3'<br>Fh8Rev:<br>5'-G T T C A C A T A A T A C A C A A T G G T A C C C T A-3' | 1 min. at 95° C., followed by 30 cycles of amplification (45 s at 94° C., 30 s at 50° C. and 45 s at 72° C.). 11 min. at 72° C. |

TABLE 1-continued

List of PCR reactions performed to obtain constructs used to evaluate the fragment H activity, DNA samples, primers and PCR program

| Purpose | DNA sample used as template | primers used | PCR program |
|---|---|---|---|
| Obtaining of Fh8RSac | Plasmid DNA-vector pQE30 containing the sequence of DNA coding for Fh8 | HFwd: 5'-G G A T C C A T G C C T A G T G T T C A A-3' Fh8RSac: 5'-G T T C A C A T A A T A C A C A A T C T G G A G C T C T G A T G A C A A A A T C-3' | 1 min. at 95° C., followed by 30 cycles of amplification (45 s at 94° C., 30 s at 50° C. and 45 s at 72° C.). 11 min. at 72° C. |
| Obtaining of Fragment CWG | Genomic DNA of *Giardia lamblia* | CWGFwd: 5'-A T C T C T T C G A G C T C C C T T A C A T G A T G-3' CWGRev: 5'-A C A G A G C T G G T A C C C T A G A C C G T C T T-3' | 4 min. at 95° C., followed by 45 cycles of amplification (30 s at 94° C., 30 s at 55° C. e 1 min at 72° C.). 7 min. at 72° C. |
| Obtaining of Fragment CP12 | Genomic DNA of *Cryptosporidium Parvum* | CP12Fwd: 5'-C A T A C T G G T A T G A G C T C G A A G G A G T A C-3' CP12Rev: 5'-C A T T A A A A G G T ACCTTTCATTATCAAG-3' | 4 min. at 95° C., followed by 30 cycles of amplification (45 s at 94° C., 30 s at 50° C. and 45 s at 72° C.). 11 min. at 72° C. |
| Obtaining of fragment HCP12 | Ligation between the PCR product that corresponds to fragment H digested with Sac I and the PCR product corresponding to the fragment CP12 digested with Sac I | HFwd: 5'-G G A T C C A T G C C T A G T G T T C A A-3' CP12Rev: 5'-C A T T A A A A G G T A C C T T T C A T T A T C A A G-3' | 4 min. at 95° C., by 30 cycles of amplification (30 s at 95° C., 30 s at 55° C. e 45 s at 72° C.). 7 min. at 72° C. |
| Obtaining of fragment FCP12 | Ligation between the PCR product that corresponds to fragment Fh8RSac digested with Sac I and the PCR product corresponding to the fragment CP12 digested with Sac I | HFwd: 5'-G G A T C C A T G C C T A G T G T T C A A-3' CP12Rev: 5'-C A T T A A A A G G T A C C T T T C A T T A T C A A G-3' | 4 min. at 95° C., followed by 45 cycles of amplification (30 s at 94° C., 30 s at 55° C. e 1 min at 72° C.). 7 min. at 72° C. |
| Obtaining of Fragment BG | Genomic DNA of *Giardia lamblia* | BGFwd: 5'-**T A A G A A A A T G A G C T C A T G T C T A T G T**-3' BGRev: 5'-**G A T T T A C T G C G G T A C C T T A G T G C T T**-3' | 4 min. at 95° C., followed by 45 cycles of amplification (30 s at 94° C., 30 s at 55° C. e 1 min at 72° C.). 7 min. at 72° C. |
| Obtaining of Fragment Ent | Genomic DNA of *Entamoeba hystolitica* | EntFwd: 5'-T C C A G T C A A T G A G C T C G A A G T G A-'3 EntRev: 5'-A T A A C A T G G G G T A C C C T A A C C A A T-'3 | 4 min. at 95° C., followed by 45 cycles of amplification (30 s at 94° C., 30 s at 55° C. e 1 min at 72° C.). 7 min. at 72° C. |
| Obtaining of Fragment Pfsp | Genomic DNA from *Plasmodium falciparum* | PfspFor: 5'-G A A G G T G T T G A G C T C G G C A C A T G T-'3 PfspRev: 5'-C C A A T A G T A G G T A C C T T A A T C A T C T G G-'3 | 4 min. at 95° C., followed by 45 cycles of amplification (30 s at 94° C., 30 s at 55° C. e 1 min at 72° C.). 7 min. at 72° C. |
| Obtaining of Fragment IL5 | Human genomic DNA | IL5Fwd: 5'-T T C A G A G C C G A G C T C A T G A G G A T G C-3' | 4 min. at 95° C., followed by 30 cycles of amplification (30 s at 95° C., 30 s at 50° C. e 45 s at 72° C.). |

TABLE 1-continued

| List of PCR reactions performed to obtain constructs used to evaluate the fragment H activity, DNA samples, primers and PCR program | | | |
|---|---|---|---|
| Purpose | DNA sample used as template | primers used | PCR program |
| | | IL5Rev: 5'-A A G A A A A T T A C G G T A C C T T A C T C A T T G G C-3' | 7 min. at 72° C. |
| Obtaining of fragment HIL5 | Ligation between the PCR product that corresponds to fragment H digested with Sac I and the PCR product corresponding to the fragment IL5 digested with Sac I | HFwd: 5'-G G A T C C A T G C C T A G T G T T C A A-3' IL5Rev: 5'-A A G A A A A T T A C G G T A C C T T A C T C A T T G G C-3' | 4 min. at 95° C., followed by 30 cycles of amplification (30 s at 95° C., 30 s at 55° C. e 45 s at 72° C.). 7 min. at 72° C. |
| Obtaining of fragment FIL5 | Ligation between PCR uct corresponding to ment Fh8RSac digested Sac I and the PCR product esponding to the fragment digested with Sac I | HFwd: 5'-G G A T C C A T G C C T A G T G T T C A A-3' IL5Rev: 5'-A A G A A A A T T A C G G T A C C T T A C T C A T T G G C-3' | 4 min. at 95° C., followed by 30 cycles of amplification (30 s at 95° C., 30 s at 55° C. e 45 s at 72° C.). 7 min. at 72° C. |
| Obtaining of Fragment Toxo | Genomic DNA of *Toxoplasma gondii* | Toxo_SacI: 5'-T G T G C C T G T G T G A G C T C C C T C C T G T G-3' Toxo_KpnI: 5'-T G A T G C G C G G T A C C C T A G G G A A C G A C-3' | 4 min. at 95° C., followed by 30 cycles of amplification (30 s at 95° C., 30 s at 50° C. e 45 s at 72° C.). 7 min. at 72° C. |
| Obtaining of fragment HToxo | Ligation between the PCR product that corresponds to fragment H digested with Sac I and the PCR product corresponding to the fragment Toxo digested with Sac I | HFwd: 5'-G G A T C C A T G C C T A G T G T T C A A-3' Toxo_KpnI: 5'-T G A T G C G C G G T A C C C T A G G G A A C G A C-3' | 4 min. at 95° C., followed by 30 cycles of amplification (30 s at 95° C., 30 s at 55° C. e 45 s at 72° C.). 7 min. at 72° C. |
| Obtaining of Fragment PAL | Genomic DNA of *Legionella pneumophila* | PALFor: 5'-T A A G G A G A T G A G C T C A T G A A A G C C-3' PALRev: 5'-A T T T T T T G C G G T A C C T C A T C T T G T T G C-3' | 4 min. at 95° C., followed by 30 cycles of amplification (30 s at 95° C., 30 s at 55° C. e 45 s at 72° C.). 7 min. at 72° C. |

TABLE 2

| Description of the protocol | | | |
|---|---|---|---|
| Antigen | Group | Experiment day | Type of animal manipulation |
| CWG | CWG group; HCWG group; FCWG group | D. 0-1ª IP | 1ª injection intraperitoneal |
| | | D. 24 after 1ª IP | 2ª injection intraperitoneal; blood collect |
| | | D. 39 after 1ª IP | 3ª injection intraperitoneal; blood collect |
| | | D. 53 after 1ª IP | blood collect |
| | | D. 59 after 1ª IP | 4ª injection intraperitoneal |
| | | D. 71 after 1ª IP | blood collect |
| | | D. 84 after 1ª IP | 5ª injection intraperitoneal |
| | | D. 93 after 1ª IP | blood collect |
| | | D. 105 after 1ª IP | 6ª injection intraperitoneal |

TABLE 2-continued

| Description of the protocol | | | |
|---|---|---|---|
| Antigen | Group | Experiment day | Type of animal manipulation |
| | | D. 114 after 1ª IP | 7ª injection intraperitoneal |
| | | D. 151 after 1ª IP | blood collect |
| | | D. 197 after 1ª IP | blood collect |
| | negative group | D. 24 after 1ª IP | blood collect |
| | | D. 39 after 1ª IP | blood collect |
| | | D. 53 after 1ª IP | blood collect |
| | | D. 71 after 1ª IP | blood collect |
| | | D. 93 after 1ª IP | blood collect |
| | | D. 151 after 1ª IP | blood collect |

TABLE 2-continued

| Description of the protocol | | | |
|---|---|---|---|
| Antigen | Group | Experiment day | Type of animal manipulation |
| | | D. 197 after $1^a$ IP | blood collect |
| CP12 | CP12 group; HCP12 group | D. 0-$1^a$ IP | $1^a$ injection intraperitoneal |
| | | D. 7 after $1^a$ IP | $2^a$ injection intraperitoneal; blood collect |
| | | D. 14 after $1^a$ IP | $3^a$ injection intraperitoneal |
| | | D. 21 after $1^a$ IP | $4^a$ injection intraperitoneal; blood collect |
| | | D. 28 after $1^a$ IP | $5^a$ injection intraperitoneal |
| | | D. 35 after $1^a$ IP | $6^a$ injection intraperitoneal; blood collect |
| | | D. 42 after $1^a$ IP | $7^a$ injection intraperitoneal; blood collect |
| | | D. 49 after $1^a$ IP | $8^a$ injection intraperitoneal; blood collect |
| | | D. 56 after $1^a$ IP | blood collect |
| | negative group | D. 7 after $1^a$ IP | blood collect |
| | | D. 21 after $1^a$ IP | blood collect |
| | | D. 35 after $1^a$ IP | blood collect |
| | | D. 42 after $1^a$ IP | blood collect |
| | | D. 49 after $1^a$ IP | blood collect |
| | | D. 56 after $1^a$ IP | blood collect |
| BG | HBG group | D. 0-$1^a$ IP | $1^a$ injection intraperitoneal |
| | | D. 11 after $1^a$ IP | $2^a$ injection intraperitoneal |
| | | D. 22 after $1^a$ IP | $3^a$ injection intraperitoneal |
| | | D. 41 after $1^a$ IP | $4^a$ injection intraperitoneal; blood collect |
| | | D. 62 after $1^a$ IP | $5^a$ injection intraperitoneal; blood collect |
| | | D. 117 after $1^a$ IP | $6^a$ injection intraperitoneal; blood collect |
| | | D. 142 after $1^a$ IP | $7^a$ injection intraperitoneal; blood collect |
| | | D. 165 after $1^a$ IP | blood collect |
| | | D. 188 after $1^a$ IP | blood collect |
| | negative group | D. 41 after $1^a$ IP | blood collect |
| | | D. 62 after $1^a$ IP | blood collect |
| | | D. 117 after $1^a$ IP | blood collect |
| | | D. 142 after $1^a$ IP | blood collect |
| | | D. 165 after $1^a$ IP | blood collect |
| | | D. 188 after $1^a$ IP | blood collect |
| Ent | Hent group | D. 0-$1^a$ IP | $1^a$ injection intraperitoneal |
| | | D. 15 after $1^a$ IP | $2^a$ injection intraperitoneal; blood collect |
| | | D. 36 after $1^a$ IP | $3^a$ injection intraperitoneal; blood collect |
| | | D. 69 after $1^a$ IP | $4^a$ injection intraperitoneal; blood collect |
| | | D. 81 after $1^a$ IP | $5^a$ injection intraperitoneal; blood collect |
| | | D. 106 after $1^a$ IP | $6^a$ injection intraperitoneal; blood collect |
| | | D. 132 after $1^a$ IP | $7^a$ injection intraperitoneal; blood collect |
| | | D. 155 after $1^a$ IP | blood collect |

TABLE 2-continued

| Description of the protocol | | | |
|---|---|---|---|
| Antigen | Group | Experiment day | Type of animal manipulation |
| | | D. 178 after $1^a$ IP | blood collect |
| | | D. 225 after $1^a$ IP | blood collect |
| | negative group | D. 15 after $1^a$ IP | blood collect |
| | | D. 36 after $1^a$ IP | blood collect |
| | | D. 69 after $1^a$ IP | blood collect |
| | | D. 81 after $1^a$ IP | blood collect |
| | | D. 106 after $1^a$ IP | blood collect |
| | | D. 132 after $1^a$ IP | blood collect |
| | | D. 155 after $1^a$ IP | blood collect |
| | | D. 178 after $1^a$ IP | blood collect |
| | | D. 225 after $1^a$ IP | blood collect |
| Pfsp | HPfsp group | D. 0-$1^a$ IP | $1^a$ injection intraperitoneal |
| | | D. 10 after $1^a$ IP | $2^a$ injection intraperitoneal; blood collect |
| | | D. 24 after $1^a$ IP | $3^a$ injection intraperitoneal |
| | | D. 42 after $1^a$ IP | $4^a$ injection intraperitoneal; blood collect |
| | | D. 49 after $1^a$ IP | $5^a$ injection intraperitoneal; blood collect |
| | | D. 61 after $1^a$ IP | $6^a$ injection intraperitoneal; blood collect |
| | | D. 70 after $1^a$ IP | $7^a$ injection intraperitoneal; blood collect |
| | | D. 84 after $1^a$ IP | blood collect |
| | | D. 152 after $1^a$ IP | blood collect |
| | negative group | D. 10 after $1^a$ IP | blood collect |
| | | D. 42 after $1^a$ IP | blood collect |
| | | D. 49 after $1^a$ IP | blood collect |
| | | D. 61 after $1^a$ IP | blood collect |
| | | D. 70 after $1^a$ IP | blood collect |
| | | D. 84 after $1^a$ IP | blood collect |
| | | D. 152 after $1^a$ IP | blood collect |
| IL5 | HIL5 group | D. 0-$1^a$ IP | $1^a$ injection intraperitoneal |
| | | D. 48 after $1^a$ IP | $2^a$ injection intraperitoneal |
| | | D. 79 after $1^a$ IP | $3^a$ injection intraperitoneal |
| | | D. 93 after $1^a$ IP | $4^a$ injection intraperitoneal; blood collect |
| | | D. 106 after $1^a$ IP | $5^a$ injection intraperitoneal; blood collect |
| | | D. 128 after $1^a$ IP | $6^a$ injection intraperitoneal; blood collect |
| | | D. 149 after $1^a$ IP | blood collect |
| | negative group | D. 93 after $1^a$ IP | blood collect |
| | | D. 106 after $1^a$ IP | blood collect |
| | | D. 128 after $1^a$ IP | blood collect |
| | | D. 149 after $1^a$ IP | blood collect |

TABLE 2-continued

| Description of the protocol | | | |
|---|---|---|---|
| Antigen | Group | Experiment day | Type of animal manipulation |
| Toxo | Htoxo group | D. 0-$1^a$ IP | $1^a$ injection intraperitoneal |
| | | D. 7 after $1^a$ IP | $2^a$ injection intraperitoneal; blood collect |
| | | D. 14 after $1^a$ IP | $3^a$ injection intraperitoneal |
| | | D. 21 after $1^a$ IP | $4^a$ injection intraperitoneal; blood collect |
| | | D. 28 after $1^a$ IP | blood collect |
| | negative group | D. 7 after $1^a$ IP | blood collect |
| | | D. 21 after $1^a$ IP | blood collect |
| CD4 | HCD4 group | D. 0-$1^a$ IP | $1^a$ injection intraperitoneal |
| | | D. 10 after $1^a$ IP | $2^a$ injection intraperitoneal; blood collect |
| | | D. 24 after $1^a$ IP | $3^a$ injection intraperitoneal |
| | | D. 42 after $1^a$ IP | $4^a$ injection intraperitoneal; blood collect |
| | | D. 49 after $1^a$ IP | $5^a$ injection intraperitoneal; blood collect |
| | | D. 61 after $1^a$ IP | $6^a$ injection intraperitoneal; blood collect |
| | | D. 70 after $1^a$ IP | $7^a$ injection intraperitoneal; blood collect |
| | | D. 84 after $1^a$ IP | blood collect |
| | | D. 152 after $1^a$ IP | blood collect |
| | negative group | D. 10 after $1^a$ IP | blood collect |
| | | D. 42 after $1^a$ IP | blood collect |
| | | D. 49 after $1^a$ IP | blood collect |
| | | D. 61 after $1^a$ IP | blood collect |
| | | D. 70 after $1^a$ IP | blood collect |
| | | D. 84 after $1^a$ IP | blood collect |
| | | D. 152 after $1^a$ IP | blood collect |
| PAL | HPAL group | D. 0-$1^a$ IP | $1^a$ injection intraperitoneal |
| | | D. 7 after $1^a$ IP | $2^a$ injection intraperitoneal; blood collect |
| | | D. 14 after $1^a$ IP | $3^a$ injection intraperitoneal |
| | | D. 21 after $1^a$ IP | blood collect |
| | negative group | D. 7 after $1^a$ IP | blood collect |
| | | D. 21 after $1^a$ IP | blood collect |
| Frut | Hfrut group | D. 0-$1^a$ IP | $1^a$ injection intraperitoneal |
| | | D. 19 after $1^a$ IP | $2^a$ injection intraperitoneal |
| | | D. 29 after $1^a$ IP | $3^a$ injection intraperitoneal |
| | | D. 37 after $1^a$ IP | $4^a$ injection intraperitoneal |
| | | D. 45 after $1^a$ IP | $5^a$ injection intraperitoneal; blood collect |
| | | D. 51 after $1^a$ IP | $6^a$ injection intraperitoneal; blood collect |
| | | D. 59 after $1^a$ IP | blood collect |
| | negative group | D. 45 after $1^a$ IP | blood collect |
| | | D. 51 after $1^a$ IP | blood collect |
| | | D. 59 after $1^a$ IP | blood collect |

PCR reactions, as well as DNA templates used for the preparation of the various fragments were performed under the conditions described in Table 1. For the preparation of genomic DNA was used the kit to extract DNA QIAamp DNA mini kit from Qiagen following the manufacturer's protocol.

The thermal cycler used for all PCR reactions was the My Cycler™ Thermal Cycler (BioRad).

The mixture of PCR reactions carried out consisted of 1 μl of sample (template DNA), 2 μl of magnesium chloride, 1 μl dNTPs (Roche), 1 μl of forward primer and 1 μl of reverse primer, 5 μl of buffer Taq polymerase (Thermo Scientific), 1 unit/reaction of Taq polymerase (Thermo Scientific) and distilled water to complete a final volume of 50 μl.

Constructs Made with the Examples Described:

The PCR products were cloned into pGEM vector and after digestion with restriction enzymes SacI and KpnI were subcloned into the vector pQE30, pQE30 containing the fragment H (pQEH) or pQE30 containing the fragment FH8 (pQEF), digested with SacI and KpnI.

Extraction and Purification of DNA from Agarose Gels

To isolate PCR products and DNA bands resulting from digestion with restriction enzymes from gel electrophoresis, we used the Illustra™ GFX PCR DNA & Gel Band Purification kit (GE Healthcare), following the procedure described by the manufacturer.

Ligation to Vector pGEM

The binding reaction to the vector pGEM-T Easy consisted in the mixing of 3 μl of DNA sample (PCR product or digestion with restriction enzymes), with 1 μl of the vector pGEM-T Easy (Promega), 5 μl of enzyme buffer 2×DNA ligase (Promega) and 1 μl of enzyme T4 DNA ligase (Promega) to a final volume of 10 μl. This reaction occurred at room temperature overnight or for 1 hour and 30 minutes at 37° C.

Confirmation of Transformants by Digestion with Restriction Enzymes

After the ligase reaction to the vector pGEM, we transformed *E. coli* XL1 Blue with the product. The cells were then spread on plates of LB/Ampicillin/X-Gal/IPTG and incubated overnight at 37° C. The transformed clones that were used to prepare liquid cultures in LB/ampicillin and subsequently to perform the extraction of plasmid DNA from *E. coli.*

The presence of targeted DNA fragments was performed by digestion with restriction enzyme EcoRI (Promega), for each reaction we used 7 μl of the plasmid DNA, 2 μl of H 10× buffer and 1 μl of EcoRI, giving a final volume of 10 μl. The reaction occurred for 2 to 3 hours at 37° C., and the result of digestion was displayed on agarose gel with appropriate percentage (w/v).

Ligation to Vector pQE

The inserts resulting from digestion with restriction enzymes were inserted into the vector pQE, pQEH or pQEFh8 by mixing 6 μl of insert with 2 μl of vector pQE, 1 μl of 10× ligase buffer (Promega) and 1 μl enzyme 14 DNA ligase (Promega). This reaction occurred at room temperature overnight or for 1 hour and 30 minutes at 37° C.

After connecting the insert to the vector, *E. coli* M15 [pREP4] were transformed with thereacyion product. The cells were then spread on plates of LB/Ampicillin/Kanamycin and incubated overnight at 37° C. The transformants were transferred to liquid cultures of LB/ampicillin/kanamycin and subsequently used to extract plasmid DNA from *E. coli.*

Confirmation of transformants was performed by digestion with restriction enzymes KpnI and BamHI (Promega). First, digestion with KpnI was performed, mixing 26 μl of plasmid DNA, 3 μl of buffer J 10× (Promega) and 1 μl of KpnI (Promega) for a final volume of 30 μl. 10 μl of digestion was analyzed on agarose gel and afterwards we proceeded to the second digestion with BamHI, for that purpose we added to the remaining first reaction, 2 μl of 10× buffer K (Promega) and 1 μl of BamHI (Promega). The result of digestion was visualized on agarose gel with appropriate percentage (w/v).

Sequencing of the Constructs Made

All the constructions made with the inserts in pGEM and pQE vectors were confirmed by sequencing at Eurofins MWG Operon (Germany).

Expression and Isolation of Recombinant Proteins

A pre-culture of 200 ml, were put to grow overnight at 37° C. with stirring, and used to prepare 2 liters of induced culture by placing 100 ml of saturated culture and 900 ml of LB medium containing 100 g/ml ampicillin, 50 g/ml kanamycin and 1 mM IPTG. After 5 hours incubation we proceeded to collect the cells by centrifuging 20 minutes at 4000 rpm at 4° C. The cell lysis was performed by incubation of cells with 40 mL of 8 M urea, pH 8.0, leaving under stirring overnight. The extract was centrifuged at 13,000 rpm for 15 minutes at room temperature and the supernatant collected. After recovery, the supernatant was filtered by a column of glass wool and applied to the column of Ni-NTA (Amersham Biosciences), pre-equilibrated with 8M urea, pH 8.0.

The supernatant was passed by the column by gravity, the column was washed with 5 CV (column volumes) of buffer 8 M urea, pH 8.0, followed by 5 CV of buffer 8 M urea with 10% glycerol, pH 6.5. Elution was done with buffer 8 M urea, pH 4.5, and 4 mL fractions were collected. The protein content of the eluted fractions was quantified by the Bradford method and fractions were analyzed in SDS-PAGE Tris-Tricine, as is described below.

Protein Quantification

The protein quantification was performed by Bradford method, with the Protein Assay reagent (BioRad) diluted 1:5, and to read the optical density at a wavelength of 595 nm. The calibration curve was obtained by reading the optical density at 595 nm of solutions of known concentration of bovine serum albumin (BSA) with this reagent.

Preparation of Inocula:

The recombinant proteins used for the demonstrations described, except HLEC were isolated under denaturing conditions in 8 M Urea. After protein quantification and analysis of the fractions, we proceeded to extensive dialysis against PBS buffer prepared with nonpyrogenic water. After dialysis we performed the filtration of protein (under non-denaturing) using a 0.2 u filter to sterilize. The volume of inoculum was hit with a 500 ul sterile nonpyrogenic PBS. The amount of protein administered varied between different samples, between 10 and 50 μg, as described above for each case. The recombinant protein HLEC was prepared in 8M urea and was dialysed against PBS buffer containing 50 mM urea, prepared with apyrogenic water, afterwards the antigens was concentrated using centricon (Amicon) membrane with cut off of 3 kDa. Inocula were prepared extemporaneously by diluting the concentrated protein in the appropriate volume of sterile PBS, non-pyrogenic, to ensure that the concentration of urea is less than 10 mM, and held the filtration of the inoculum through a filter pyrogenic 0, 2μ.

Tests in Mice:

Experiments carried out in this work were performed in models of CD1 mice obtained from Charles River SA Barcelona. The animals were housed and maintained with food and drink ad libitum. The maintenance and care of animals were made in accordance with existing directives. Each group consists of 3 mice and inoculation was administered intraperitoneally periodically, according to the protocols described in Table 2, blood sampling have been conducted periodically at the tail vein, according to the protocols described in Table 2. After collecting the blood, serum was obtained by centrifugation at 2500 rpm for 10 min and kept in the at −20° C.

Electrophoresis in Polyacrylamide Gel SDS-PAGE Tris-Tricine

The Tris-Tricine gels used to analyze the collected fractions were based on Tris-Tricine system of Schägger, H. and Jagow, G. (1987) and SDS-PAGE of Laemmli (1970). Thus, the system adopted consisted of two gels: one resolvent gel of 15% and a packaging gel of 4%. The resolvent gel contained 3.3 mL 30% acrylamide, 2.205 mL of gel, 705 mL of glycerol, 367.5 mL of water, 150 μl of PSA 10% and 9 μl of TEMED. The gel packing contained 700 μl of 30% acrylamide, 1.25 mL of gel, 3 mL of water, 200 μl of 10% PSA and 5 μl of TEMED.

The electrophoresis system used was composed of two reservoirs, higher (from the gels) and bottom, in which were placed the cathode buffer and anode buffer, respectively. We applied a potential difference (DDP) of 100 V to the gel packaging and a ddp of 150 volts for the resolvent gel.

Samples (in native or denaturing conditions) before being applied to the gel, were treated with sample buffer Tris-Tricine 1×. Samples in native conditions were also placed in the bath at 100° C. for 2 minutes, after getting to 4° C. until loaded on the gel.

The gels were stained with Coomassie Blue.

Transfer to Nitrocellulose Membranes

We dipped into transfer buffer (25 mM Tris, 0.2 M glycine, 100 ml methanol), 2 filter papers, the nitrocellulose membrane, the SDS-PAGE in which proteins ran, and sponges needed for assembly of the sandwich. After soaked in buffer we proceeded to mount the sandwich, and transfer was performed using system TE 80 (Hoefer). The transfer took place in transfer buffer, for 1 h at a constant potential difference of 80V.

Immunoblotting

After the transfer, 0.45 μm, μnitrocellulose membrane (Schleicher & Schell) was saturated with PBS-milk 5%, for 1 h at room temperature. He washed the membrane with 2×PBS-0.3% Tween (PBS-T). Incubated the membrane with sera diluted in PBS-milk with the appropriate concentration, overnight at 4° C. We washed the membrane 3× with PBS-T. The conjugate protein G-peroxidase (Bio Rad) was added to diluted to 1/1000 in PBS-milk, and incubated at room temperature for 2 h. We washed the membrane 3× with PBS-T and revealed with 15 mg 4-chloro-1-naphthol dissolved in 5 ml cold methanol, 20 ml PBS and 25 μl 30% H2O2.

Immunoassay by ELISA

The "coating of microplates (Nunc) polystyrene was performed with 100 μl/per well 1 of antigen at 10 μg/ml antigen in carbonate/bicarbonate buffer 0.1 M pH 9.50N at ° C. The wells were washed with PBS-T 0.3%, then saturated with 200 μl PBS-0.1% gelatin per well at 37° C. for 30 min in moist chamber and washed again with PBS-T. We added to each well 100 μl of diluted sera at 1/400 in PBS-T and put to incubate in moist chamber overnight at 4° C. The plates were washed 3× with PBS-T. We added to each well 100 μl l of protein G-coupled peroxidase (Biorad) diluted at 1/2000 in PBS-T, and put to incubate for 1 h at 37° C. in moist chamber. The wells were washed 3× with PBS-T. The reaction of substrate contained 1 mg of OPD per ml 0.2 M phosphate pH 5.6. For each ml of this solution we added 1 μl of H2O2 30%. 100 μl of substrate was added per well and reaction was stopped with 100 μl of 3M HCl per well.

The optical density was read at 490 nm in a ELISA plate Model 680 (Biorad).

Immunofluorescence

The biological material for tests, immunofluorescence was obtained from water samples and faeces, in the case of *Cryptosporidium parvum* (CP12) and *Giardia lamblia* (CWG), for *Entamoeba histolytica* (ENT) slides were obtained from the supplier Biomérieux diagnosis, In the case of β-Giardina (BG) we used Axenic cultures of trophozoites. To prepare slides with parasitary material, sample of parasites were added to each well of the slide for immunofluorescence and left to dry in the oven until the sediment remain fixed; Were added two drops of acetone to dry completely. Left to dry at room temperature plus five more minutes in the oven 37° C. For the immunofluorescence we added 10 μl of serum (primary antibody) in the corresponding dilution, and left in a moist chamber at 37° C. about 1 hour and washed 3× with PBS. The conjugate anti-mouse IgG labeled with FITC (Sigma) diluted in PBST was added to the slide and incubated in a moist chamber for 1 h at 37° C. The slides were washed. We added the contrasting (Evans blue) solution and then 10 μl of mounting medium. The slides were observed under a microscope Nikon Optiphot immunofluorescence.

EXAMPLES

For an easier understanding of the invention are described below preferential examples of application of the invention, which, however, are not intended to limit the scope of this invention.

The recombinant antigen under study in this work is characterized by inducing an immune response that can be assessed by the production of specific polyclonal antibodies. Studies have previously indicated that the fragment H played a key role in stability and immunological characteristics of antigen FH8: antigens derived from FH8 whose sequence H had been deleted showed a drastic reduction in their stability and immunogenicity.

The strategies presented had, as starting point these assumptions, fragments were chosen in order to vary widely in heir origin, nature and immunological characteristics, as well as different application protocols intended to evaluate the use of this application in the induction of specific immune responses without the use of another constituent (adjuvant) than the antigen itself. To this end we proceeded to the selection of fragments whose immunological characteristics in the presence of adjuvants, had previously been evaluated, such as CD4 and fragments CWG that had proven to be poorly immunogenic, the fragments CP12 and LEC, which were shown to have intermediate immunogenic characteristics or the PAL that is a very immunogenic antigen, or fragments, as fragments Ent, IL5 and Pfsp whose biochemical characteristics, including family protein, molecular weight and amino acid sequence, determined that they would be poorly or non-immunogenic. Finally we also used fragments, such as Toxo and BG which immunological characteristics were completely unknown. To assess the actual impact of fragment H on the immunogenicity of the antigen to which is added we conducted demonstrations assessing the ability to induce an immune response by fragments CWG and CP12 in the absence and presence of fragment H.

Example 1

Figure 3A:
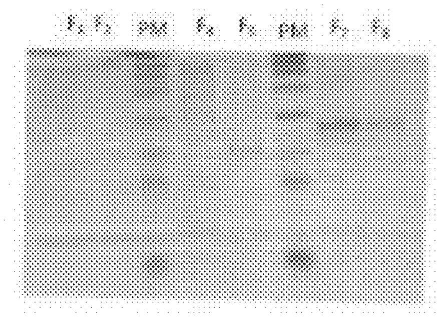
FIG. 3—Results of the demonstrations performed with the constructs containing the fragment CWG. A—SDS-PAGE Tris-Tricine stained with Coomassie Blue. PM—Marker prestained SDS-PAGE Standards (BioRad). wells F1, F2—Fractions 1, 2, of CWG collected from column Ni-NTA; Wells F4, F5—Fractions 1, 2 of HCWG collected from column Ni-NTA. Wells F7, F8—Fractions 1, 2 of FCWG collected from column Ni-NTA. B—Optical densities of ELISAs performed with sera from CD1 mice inoculated with CWG (group CWG), HCWG (group HCWG) FCWG (group FCWG) and CD1 without treatment (Group Neg). The values represent the average of optical densities of 3 CD1 used in each group. The CD1 were inoculated periodically and we carried out the collection of sera periodically, according to the protocol described in Table 2, a) Results obtained with plates containing the recombinant antigen CWG b) Results obtained with plates containing the recombinant antigen HCWG; C—Results the optical densities of ELISAs performed with sera collected from CD1 mice 83 days after the last inoculation with CWG (group CWG), HCWG (group HCWG) FCWG (group FCWG) and CD1 without treatment (Group Neg). The values represent the average of optical densities of 3 CD1 used in each group. D—Immunoblottings performed with a nitrocellulose membrane containing the recombinant antigen FCWG. FG—nitrocellulose membrane antigen FCWG stained with solution of Schwartz. PM—molecular weights. Pools of sera from negative group (a and d), the group inoculated with CWG (b and e) and inoculated with HCWG (c and f), from the harvest performed 9 days after the 5th IP (a, b and c) and after 6th IP (d, e and f) diluted at 1/200 were incubated with a strip of NC containing the antigen FCWG ON at 4° C. g and h) immunoblottings performed with sera from negative rabbit (g) and immunized against the antigen F (h) diluted at 1/100. As conjugate we used protein G-HRP diluted 1/1000 and we proceeded to revelation with 4-chloro-naphthol. E—Immunofluorescence of *Giardia lamblia* with sera from mice group HCWG. a) light microscopy, a magnification of 20×. b) UV microscopy with 20× magnification. The arrow indicates a cyst of *Giardia lamblia*

Evaluation of the Immune Response in Proteins Resulting of the Constructs with the Fragment CWG After obtaining the b constructs pQECWG, pQEHCWG and pQEFCWG we proceeded to the production and analysis of the respective recombinant antigens under denaturing conditions (FIG. 3A).

In the analysis of SDS-PAGE Tris-Tricine gels (FIG. 3A) we can see that the protein CWG has a molecular weight of 16 kDa, as expected, while the fusion protein HCWG has a weight of about 17 kDa and the recombinant antigen FCWG has a weight of about 24 kDa.

Figure 3B:
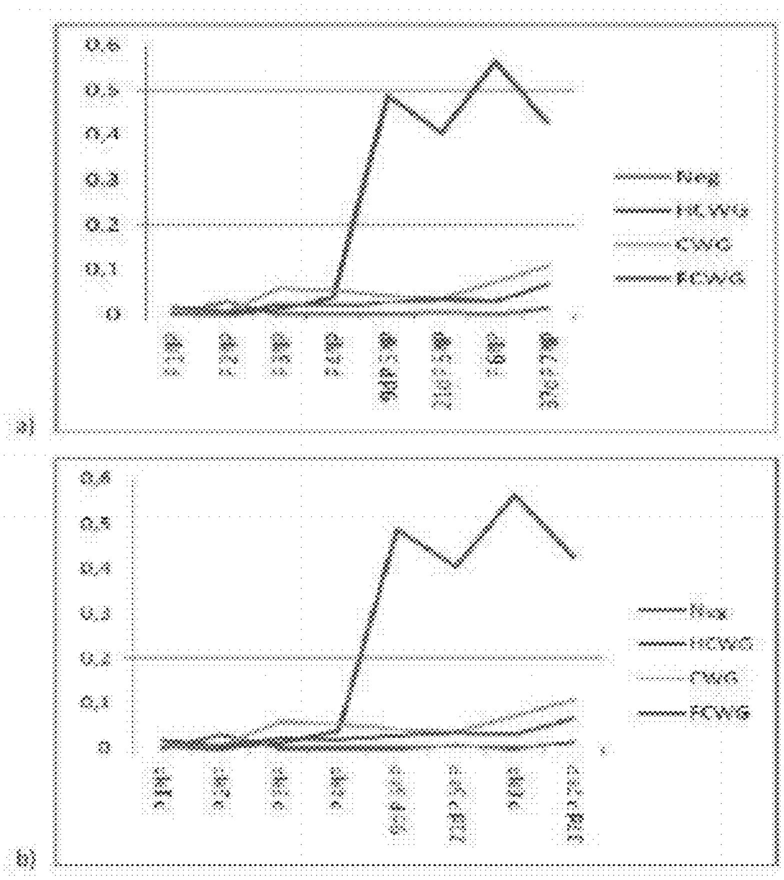
Figure 3C:
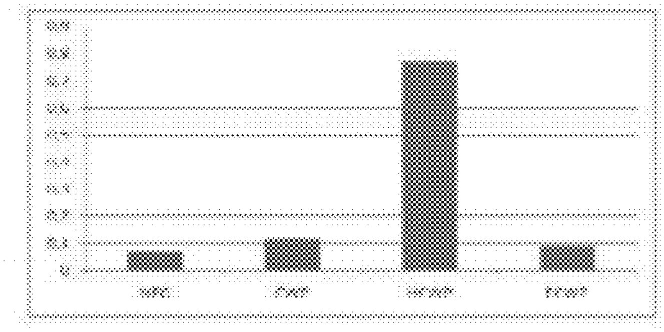
Figure 3D:
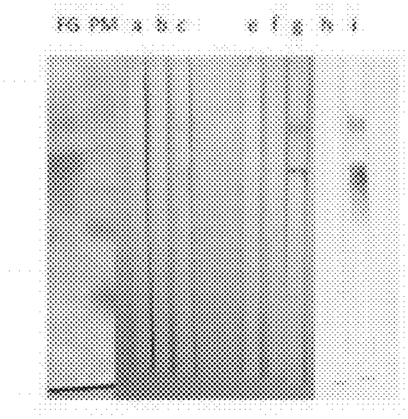
Figure 3E:
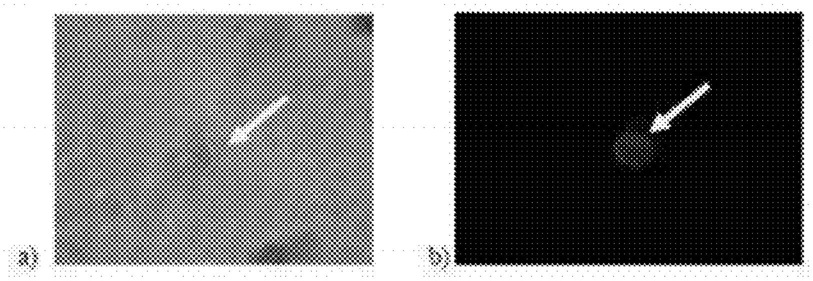

Demonstration of the effect of the presence of the fragment H on the induction of a specific immune response against the CWG has been performed by inoculation with 3 groups of CD1 mice with 50 μg of antigen CWG, HCWG and FCWG, regularly (Table 2) by IP administration. He used also a group of 3 CD1 with the same characteristics that received no inoculation. There has been regular blood collection (Table 2) for further evaluation of the presence of Ig anti-CWP. The evaluation of the presence of specific antibody response was performed by ELISA with plates containing antigens CWG (FIG. 3B.a) HCWG (FIG. 3B.b) and FCWG. There is the appearance of significant Immunoglobulin G(IgG) anti-CWG from the 4th inoculation onwards but only in the group HCWG. In group FCWG we verified the presence of IG anti-FH8 but could not confirm the presence of specific IgG against fragment CWG (data not shown). The presence of Ig G anti-CWG, in HCWG group, was detected even 83 days after the last administration indicating the existence of a specific memory for this antigen. To assess the specificity of polyclonal antibodies we performed blots using as antigen the FCWG. The location of the recombinant protein FCWG as well as possible polymers was carried out with the antisera produced against FH8 (FIG. 3D.i), diluted 1/100, that allows the viewing of polymers FCWG. Using pools of serum from negative group, CWG group and HCWG group obtained 9 days after the 5th IP and post 6th IP, diluted 1/200, the appearance of precipitates corresponding to FCWG. The realization of immunoblottings with the same dilutions using antigen FH8 (to evaluate the production of IgG anti-fragment H) didn't show no appearance of any precipitate. All these results shows that the antibodies developed by the group HCWG are specific of fragment CWG. The presence of significant cross-reactions with antigens of *E. coli* or the presence of Ig anti-fragment H is not observed. To assess whether the Ig produced were capable of recognizing the native protein existing in the wall of *Giardia* cysts we proceeded to the realization of immunofluorescence with sera from group HCWG which revealed the presence of fluorescent wall structures (FIG. 3E).

Example 2

Figure 4A:
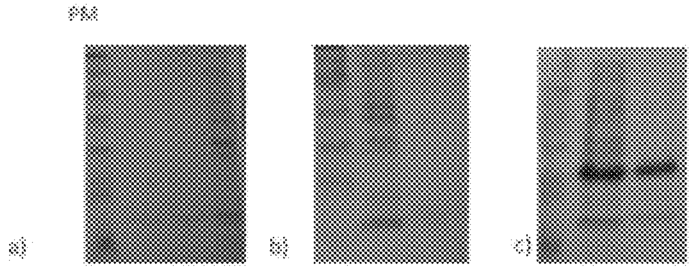
FIG. 4—Results of the demonstrations performed with the constructs containing the fragment CP12. A—SDS-PAGE Tris-Tricine gels stained with Coomassie Blue. PM—prestained marker SDS-PAGE Standards (BioRad). (a) Fractions 1, 2 and 3 of CP12 collected from column of Ni-NTA. (b) Fractions 1, 2 of HCP12 collected from column Ni-NTA. (c) Fractions 1, 2 of FCP12 collected from column of Ni-NTA; B—Optical densities of ELISAs performed with sera from CD1 mice challenged with CP12 (CP12 group), HCP12 (HCP12 group) and CD1 without treatment (Group NEG). The values represent the average of optical densities of 3 CD1 used in each group. The CD1 were inoculated periodically and we carried to collection of sera periodically, according to the protocol described in Table 2, a) Results obtained with plates containing the recombinant antigen CP12 b) Results obtained with plates containing the recombinant antigen HCP12; C—Immunoblottings performed with a nitrocellulose membrane containing the recombinant antigen FCP12. FC-nitrocellulose membrane containing the antigen FCP12 stained with solution of Schwartz. PM—molecular weights. Sera from harvest post 8th IP from negative group (g, h and i), from group inoculated with CP12 (d, e and f) and inoculated with HCP12 (a, b and c), diluted to 1/1000, were incubated with a strip containing the NC with antigen FCP12 ON at 4° C. As conjugate we used protein G-HRP diluted 1/1000 and we proceeded to revelation with 4-chloro-naphthol. The white arrow indicates the location of the antigen FCP12 determined by immunoblottings performed with sera from rabbits immunized against the antigen F. D—Immunofluorescence of *Cryptosporidium parvum* in serum of mice immunized with the protein HCP12, magnification of 20×.

Evaluation of the Immune Response for Proteins of the Constructs with the CP12 Fragment After obtaining the constructs pQECP12 and pQEHCP12 we proceeded to the production and analysis of the respective recombinant antigens under denaturing conditions (FIG. 4A).

Figure 4B:
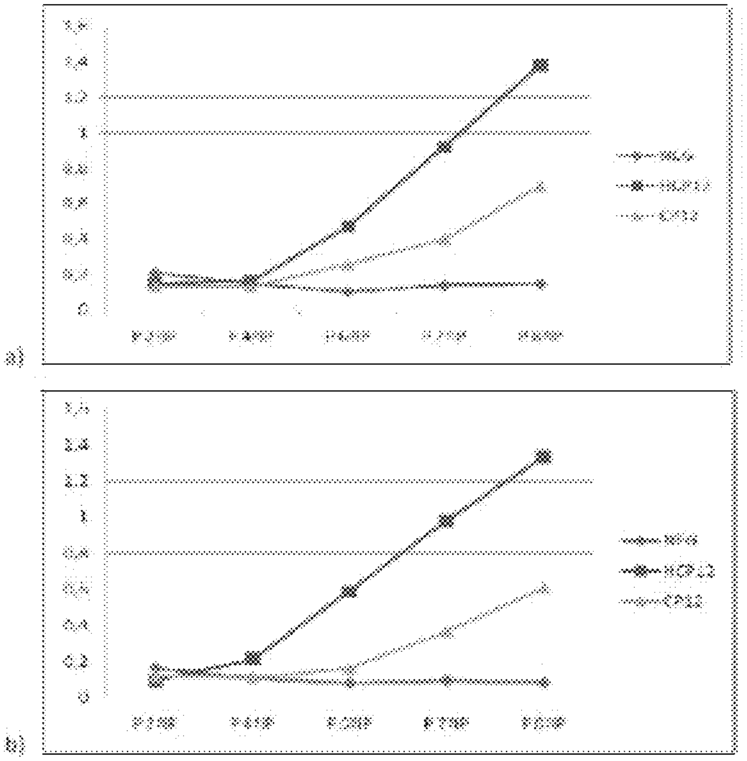

In the analysis of SDS-PAGE Tris-Tricine gels (FIG. 3A) we can see that the CP12 protein has a molecular weight of 9 kDa, as expected, while the fusion protein HCP12 has a weight of approximately 10 kDa and the recombinant antigen FCP12 presents an antigen with weight of about 29 kDa. Having regard to the PM calculated for the recombinant antigen, the band of 29 kDa may be a polymer FCP12. Demonstration of the effect of the presence of the fragment H on the induction of a specific immune response against the CP12 has been performed by inoculation with 2 groups of CD1 mice with 20 μg of antigen CP12 and HCP12 periodically (Table 2) by IP administration. We also used a group of 3 CD1 with the same characteristics that received no inoculation. There has been regular blood collection (Table 2) for further evaluation of the presence of Ig anti-CP12. The evaluation of the presence of specific antibody response was performed by ELISA with plates containing the CP12 antigen (FIG. 4B.a) HCP12 (FIG. 4B.b). There is the appearance of anti-CP12 from the 4th inoculation onwards in group HCP12, being also visible the appearance in CP12 group of Ig anti-CP12 from the 6th IP onwards. In both groups the titles of Ig anti-CP12 evolve throughout the experiment. In this example the increase of immunogenicity can be observed by the earlier immune response and the higher amount of IgG anti-CP12 present in group HCP12.

Figure 4C:
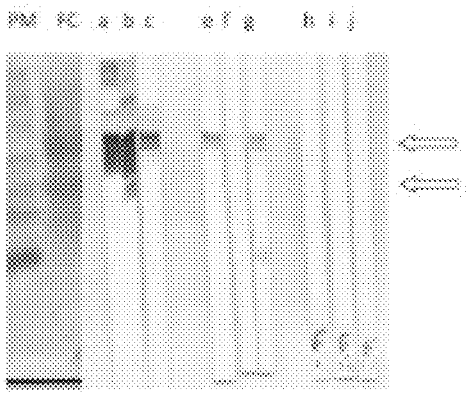
Figure 4D:
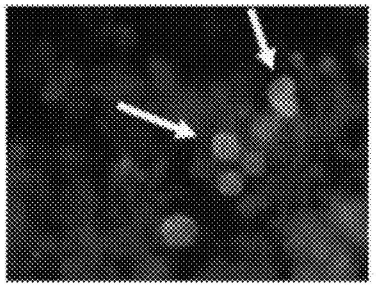

To assess the specificity of polyclonal antibodies produced we performed blots using as antigen the FCP12. The location of the recombinant protein FCP12 was carried out with the Fh8 specific antisera (FIG. 4C), diluted 1/100, that allows the viewing of FCP12 polymers, whose locations are indicated by arrows. There is, using sera from groups: negative, CP12 and HCP12, harvested post 8$^{a}$ IP, and diluted 1/1000, the appearance of precipitates corresponding to proteins identified by serum anti-FH8. The highest intensity present in HCP12 group, when compared with the CP12 group, confirms the increase of immune response that occurs in group HCP12. Immunoblottings performed with the same sera using antigen FH8 didn't show that appearance of any precipitate. All these results shows that the antibodies developed by the group HCP12 are specific to the CP12 fragment since the presence of significant cross-reactions with antigens of *E. coli* or the presence of anti-Ig fragment H is observed. To assess whether the Ig produced were capable of recognizing the native protein existing in the wall of *Cryprosporidium* oocysts we proceed to the realization of immunofluorescence with sera from group HCP12 which revealed the presence of fluorescent in wall structures (FIG. 4D).

Example 3

Evaluation of Immune Response Proteins and Fragments Resulting from the Construction with the Fragment H For each of the fragments described we proceeded to demonstration on the production of immune response inoculating 3 groups of CD1 mice with the corresponding antigen at regular intervals (Table 2) by IP administration. We also used a group of 3 CD1 with the same characteristics that received no inoculation. There has been regular blood collection (Table 2) for further evaluation of the presence of Ig directed against the target antigen.

Figure 5A:
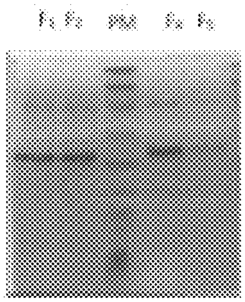
FIG. 5—Results of the demonstrations performed with the constructs containing the fragment BG. A—SDS-PAGE Tris-Tricine gel stained with Coomassie Blue. PM—Marker prestained SDS-PAGE Standards (BioRad). Wells F1, F2—Fractions 1, 2 of BG collected from column of Ni-NTA; Wells F4, F5—Fractions 1, 2, of HBG collected from column of Ni-NTA; B—Optical densities of ELISAs performed with sera CD1 mice inoculated with HBG (HBG group) and CD1 without any treatment (Group NEG). The values represent the average of optical densities of 3 CD1 used. The CD1 were inoculated periodically and we carried to the collection of sera periodically, according to the protocol described in Table 2. C—Immunoblottings performed with a nitrocellulose membrane containing the recombinant antigen BG. BG-nitrocellulose membrane containing the antigen BG stained with Schwartz solution. PM—molecular weights. Sera of harvest post 7th IP from negative group (d, e and f) of the group inoculated with HBG (a, b and c), diluted to 1/1000, were incubated with a strip of NC containing the antigen BG ON at 4° C. As conjugate we used protein G-HRP diluted 1/1000 and we proceeded to revelation with 4-chloro-naphthol. D—Immunofluorescence with *Giardia lamblia* using serum from mice of group HBG. a) normal microscopy, a magnification of 40×. b) UV microscopy with magnification of 40×. The arrow indicates two trophozoites of *Giardia lamblia.*
Figure 5B:
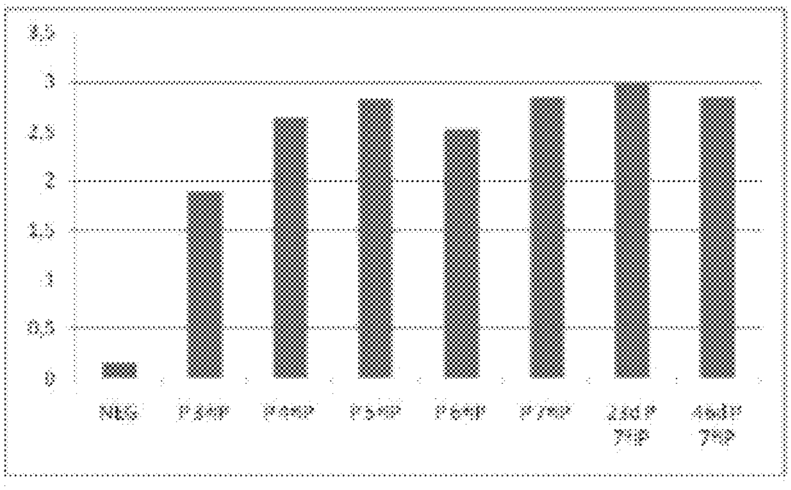
Figure 5C:
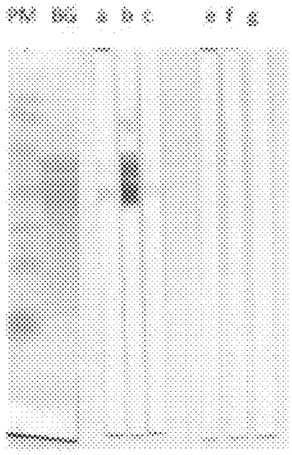
Figure 5D:
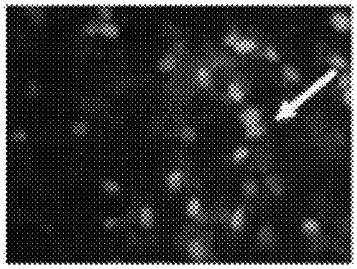

Protein BG: The immunological features on this fragment were unknown. After obtaining the construct pQEHBG we proceeded to the production and analysis of the respective recombinant antigens (FIG. 5A). Demonstration of the effect of the presence of the fragment H on the induction of a specific immune response against the BG has been performed by inoculation a groups of 3 CD1 mice with 20 μg of antigen HBG. The evaluation of the presence of specific antibody response was performed by ELISA with plates containing the antigen HBG (FIG. 5B). There is the appearance of Ig G anti-BG from the 3rd inoculation onwards. The antibody levels reach a plateau after the 4th IP that has been maintained even 47 days after last inoculation.

To assess the specificity of produced polyclonal antibodies we performed blots using as antigen the BG. There is, using the sera from negative and HBG groups harvested post 7th IP, diluted 1/1000, the appearance of precipitates corresponding to BG. The presence of significant cross-react with antigens of *E. Coli* was not detected. To assess whether the Ig produced were capable of recognizing the native protein existing in the wall of *Giardia* we considered the realization of immunofluorescence with sera from group HBG which revealed the presence of immunofluorescence in the wall of these structures. Protein fragment Ent: Due to the low molecular weight of this polypeptide (7 Kda) and since it represents only a portion of a protein, this fragment had characteristics associated with low immunogenicity.

After obtaining the construct pQEHEnt we proceeded to the production and analysis of their recombinant antigens. Demonstration of the production of immune response was performed proceeding to inoculations of 3 CD1 mice with 50 μg of HEnt antigen. The evaluation of the presence of specific antibody response was performed by ELISA with plates containing the antigen HEnt (FIG. 5B). There is the appearance of Ig G anti-Ent from the 5th IP onwards. The antibody levels reach a plateau after the 5th IP that was maintained even 90 days after last inoculation. To assess the specificity of polyclonal antibodies produced we performed blots using as antigen the FEnt. The recombinant protein FEnt was further identified with specific antisera anti FH8 (FIG. 6B), diluted 1/100, that allows the viewing of FEnt polymers, whose locations are indicated by arrows. There is, using the sera of negative and HEnt groups, harvested post 7 th IP, and diluted 1/1000, the appearance of precipitates, in HEnt group corresponding FEnt. Immunoblottings performed with the same sera using antigen FH8 didn't shows the appearance of precipitate. All these results shows that the antibodies developed by the group HEnt are specific of fragment Ent since the presence of significant cross-reactions with antigens of *E. coli* or the presence of anti-Ig fragment H was not detected.

Figure 6A:
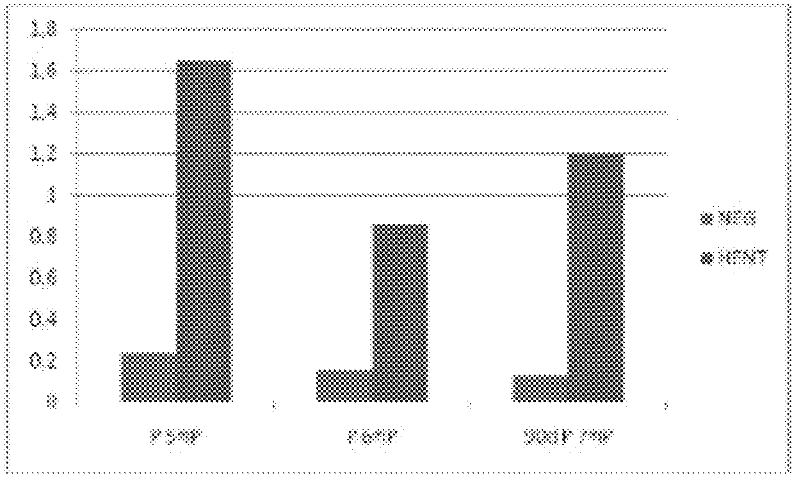
FIG. 6—Results of the demonstrations performed with the constructs containing the fragment Ent. A—Optical densities of ELISAs performed with sera from mice inoculated with CD1 HEnt (group HEnt) and CD1 without any treatment (Group NEG). The values represent the average of optical densities of 3 CD1 used. The CD1 were inoculated periodically and we carried out to sera collection periodically, according to the protocol described in Table 2. B—Immunoblottings performed with a nitrocellulose membrane containing the recombinant antigen Fent. Fent-nitrocellulose membrane containing the antigen FEnt stained with Schwartz solution. PM—molecular weights. Sera from harvest post 7th IP of negative group (a, b and c) and the group inoculated with HEnt (d, e and f), diluted to 1/1000, were incubated with a strip of NC containing the antigen FEnt ON at 4° C. As conjugate we used protein G-HRP diluted 1/1000 and we proceeded to revelation with 4-chloro-naphthol. The white arrow indicates the location of the antigen determined by FEnt immunoblottings performed with sera from rabbits immunized against the antigen F. C—Immunofluorescence with trophozoites of *Entamoeba histolytica* using serum from mice immunized with HENT, magnification 20×.
Figure 6B:
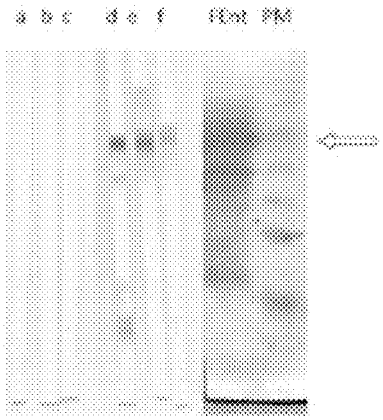

To assess whether the Ig produced were capable of recognizing the native protein existing in the wall of *Entamoeba* trophozoites we performed immunofluorescence with sera from group Hent which revealed the presence of fluorescent wall structures (FIG. 6C). Protein fragment PFSP: Due to the low molecular weight polypeptide (7 kDa) and since it represents only a portion of a protein, this fragment had characteristics associated with low immunogenicity.

After obtaining the construct pQEHPfsp we proceeded to the production and analysis of the respective recombinant antigens under denaturing conditions.

Figure 7A:
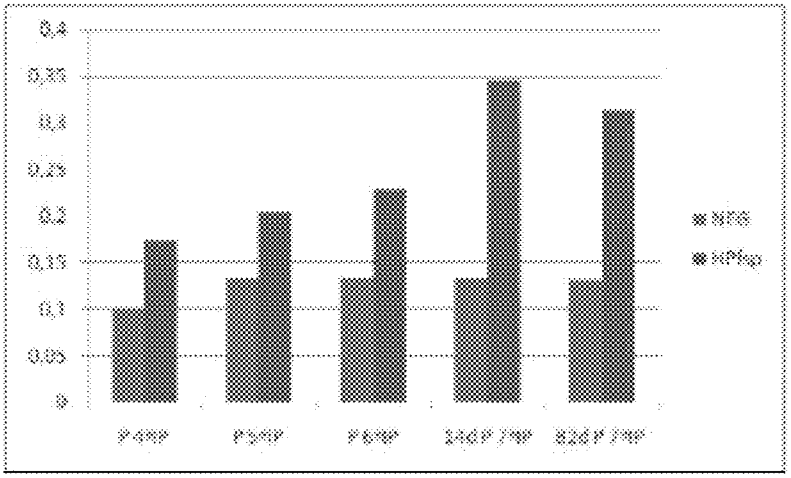
FIG. 7—Results of the demonstrations performed with the constructs containing the fragment Pfsp. A—Optical densities of ELISAs performed with sera from CD1 mice inoculated with HPfsp (group HPfsp) and CD1 without any treatment (Group NEG). The values represent the average of optical densities of 3 CD1 used. The CD1 were inoculated periodically and we carried out to sera collection periodically, according to the protocol described in Table 2. B—Immunoblottings performed with a nitrocellulose membrane containing the recombinant antigen FPfsp. Pool of sera from negative group (c), of the group inoculated with HPfsp (d and f) from harvest post 6th IP (d) and 14 days after the 7th IP (f), diluted at 1/200, were incubated with a strip of NC containing antigen FPfsp ON at 4° C. b) immunoblottings performed with sera from negative rabbit (a) and immunized against the antigen F (b) diluted to 1/100. As conjugate we used protein G-HRP diluted 1/1000 and we proceeded to revelation with 4-chloro-naphthol.
Figure 7B:
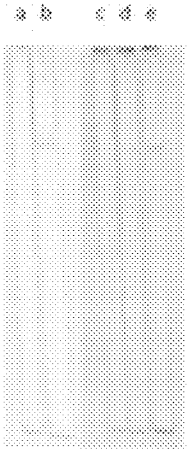

Demonstration of the production of immune response was performed proceeding to the inoculation of CD1 mice with 50 μg of antigen HPfsp. The evaluation of the presence of specific antibody response was performed by ELISA with plates containing the antigen HPfsp (FIG. 7B). There is the appearance of IgG anti-Pfsp from the 4 th IP onwards. The antibody levels reach a plateau after the 7th IP that has been maintained even 82 days after last inoculation. To assess the specificity of produced polyclonal antibodies we performed blot using as antigen the FPfsp. The recombinant protein was located with specific anti FH8 antisera (FIG. 7B.a), diluted to 1/100, that allows the viewing of FPfsp polymers. Using pool of sera from HPfsp and negative groups harvested post 6 th IP and 14 days post 7th IP, diluted 1/200, we observe the appearance of precipitates corresponding to FPfsp.

Immunoblottings performed with the same sera using antigen FH8 didn't shows the appearance of precipitate. All these results shows that the antibodies developed by the group HPfsp are specific of fragment Pfsp since the presence of significant cross-reactions with antigens of *E. coli* or the presence of anti-Ig fragment H was not detected. IL5 protein fragment: Due to the low molecular weight polypeptide (7 kDa) and since it represents only a portion of a protein with high homology with the IL of 5 mice and has been described as non immunogenic, this fragment had characteristics associated with low immunogenicity. After obtaining the construct pQEHIL5 we proceeded to the production and analysis of the respective recombinant antigens under denaturing conditions.

Figure 8A:
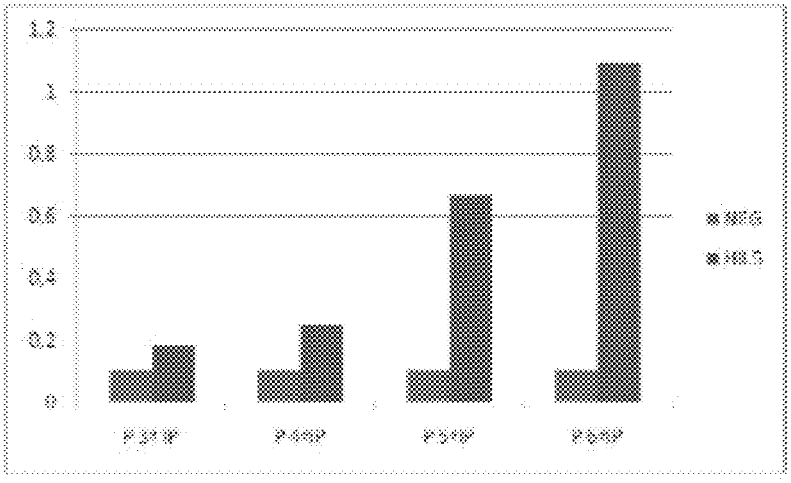
FIG. 8—Results of the demonstrations performed with the constructs containing the fragment IL5. A—Optical densities of ELISAs performed with sera from CD1 mice inoculated with HIL5 (group HIL5) and CD1 without any treatment (Group NEG). The values represent the average of optical densities of 3 CD1 used. The CD1 were inoculated periodically and we carried out to the collection of sera periodically, according to the protocol described in Table 2. B—Immunoblottings performed with a nitrocellulose membrane containing the recombinant antigen FIL5. FIL5-nitrocellulose membrane containing the antigen FIL5 stained with Schwartz solution. PM—molecular weights. Sera from harvest post 6th IP from negative group (a, b and c) and the group inoculated with HIL5 (d, e), diluted to 1/1000, were incubated with a strip of NC containing the antigen FIL5 ON at 4° C. As conjugate we used protein G-HRP diluted 1/1000 and we proceeded to revelation with 4-chloro-naphthol. The white arrow indicates the location of the antigen FIL5 determined by immunoblottings performed with sera from rabbits immunized against the antigen F.

Demonstration of the production of immune response was performed inoculating CD1 mice with about 20 μg of HIL5 (Table 2). The evaluation of the presence of specific antibody response was performed by ELISA with plates containing the antigen HIL5 (FIG. 8A). There is the appearance of Ig G anti-IL5 from the 4 th IP onwards. The antibody level grows due to the inoculations throughout the study period.

Figure 8B:
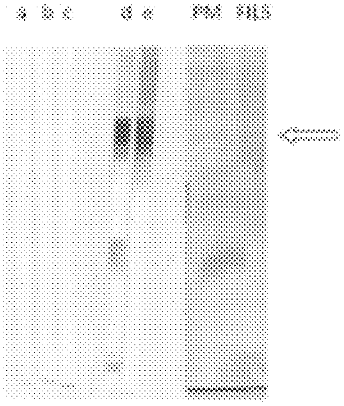

To assess the specificity of polyclonal antibodies produced we performed blots using as antigen the FIL5. The location of the recombinant protein FIL5 was carried out with the specific anti-FH8 antisera diluted to 1/100, that allows the viewing of FIL5 polymers indicated with arrow. It was found (FIG. 8B), using sera from HIL5 and negative groups obtained post 6th IP, diluted to 1/1000, the appearance of precipitates corresponding to FIL5.

Immunoblottings performed with the same sera using antigen FH8 didn't shows the appearance of precipitate. All these results shows that the antibodies developed by the group HIL5 are specific of fragment IL5 since the presence of significant cross-reactions with antigens of *E. coli* or the presence of anti-Ig fragment H was not detected. Protein Toxo: The immunological features on this fragment were unknown. After obtaining the construct pQEHToxo we proceeded to the production and analysis of their recombinant antigens.

Figure 9A:
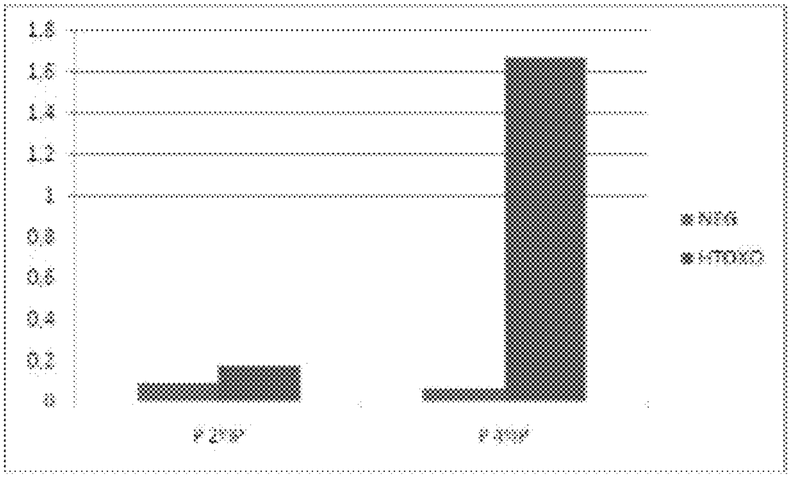
FIG. 9—Results of the demonstrations performed with the constructs containing the fragment Toxo. A—Optical densities of ELISAs performed with sera from CD1 mice inoculated with HToxo (group HToxo) and CD1 without any treatment (Group NEG). The values represent the average of optical densities of 3 CD1 used. The CD1 were inoculated periodically and we carried out to the collection of sera periodically, according to the protocol described in Table 2. B—Immunoblottings performed with a nitrocellulose membrane containing the recombinant Toxo antigen. Toxo-nitrocellulose membrane containing the antigen BG stained with Schwartz solution. PM—molecular weights. Sera from harvest post 4th IP from negative group (a, b and c), group inoculated with inoculated with HToxo (d, e and f), diluted to 1/1000, were incubated with a strip of NC containing Toxo antigen ON at 4° C. As conjugate we used protein G-HRP diluted 1/1000 and we proceeded to revelation with 4-chloro-naphthol.
Figure 9B:
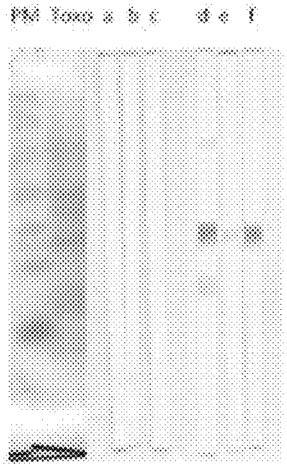

Demonstration of the production of immune response was performed by inoculating CD1 mice with 20 μg of antigen HToxo (Table 2). The evaluation of the presence of specific antibody response was performed by ELISA with plates containing the antigen HToxo (FIG. 9A). There is the appearance of IgG anti-Toxo from the 4th inoculation onwards.

Figure 10A:
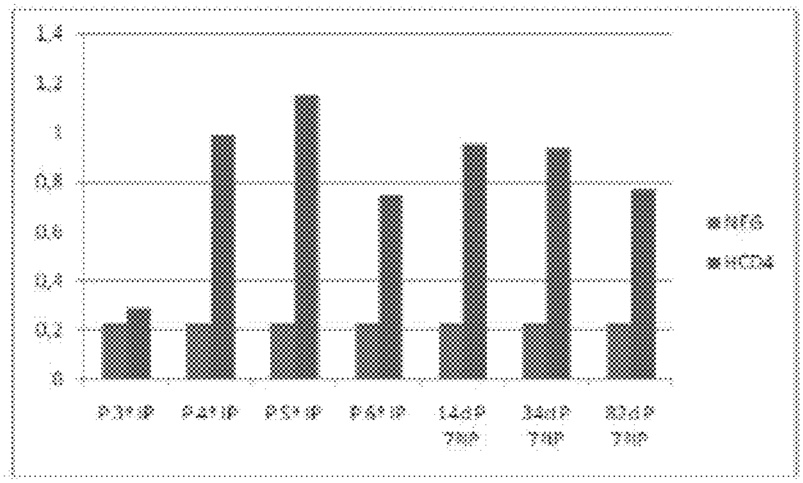
FIG. 10—Results of the demonstrations performed with the constructs containing the fragment CD4. A—Optical densities of ELISAs performed with sera from CD1 mice inoculated with HCD4 (group HCD4) and CD1 without any treatment (Group NEG). The values represent the average of optical densities from 3 CD1. The CD1 were inoculated periodically and we carried out to the collection of sera periodically, according to the protocol described in Table 2. B—Immunoblottings performed with a nitrocellulose membrane containing the recombinant antigen CD4. CD4-nitrocellulose membrane containing the CD4 antigen stained with Schwartz solution. PM—molecular weights. Pools of sera from negative group (a) and the group inoculated with HCD4 (b) of the harvest of 14 days after the 7th IP, diluted to 1/500, were incubated with a strip of NC containing the CD4 antigen ON at 4° C. As conjugate we used protein G-HRP diluted 1/1000 and we proceeded to revelation with 4-chloro-naphthol.

To assess the specificity of produced polyclonal antibodies we performed blots using as antigen Toxo. There is, using sera harvested post 4th IP, diluted at 1/1000, the appearance of precipitates corresponding to recombinant Toxo in the group HToxo. The presence of significant cross-reactions with antigens of *E. Coli* was not observed. Fragment CD4: This fragment was shown to be poorly immunogenic. After obtaining the construct pQEHCD4 we proceeded to the production and analysis of the respective recombinant antigens under denaturing conditions. Demonstration of the production of immune response was performed by inoculating CD1 mice with 30 μg of antigen HCD4 (Table 2). The evaluation of the presence of specific antibody response was performed by ELISA with plates containing the antigen HCD4 (FIG. 10A). There is the appearance of anti-CD4 from the 4th inoculation onwards. The antibody levels reach a plateau after the 4th IP that remains 82 days after last inoculation.

Figure 10B:
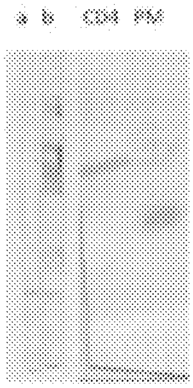

To assess the specificity of produced polyclonal antibodies we performed blots using as antigen the recombinant CD4. Using a pool of sera harvested 14 days after the 7th IP and diluted 1/500, the appearance of precipitates corresponding to CD4 is observed in the group HCD4, (FIG. 10 B).

Figure 11A:
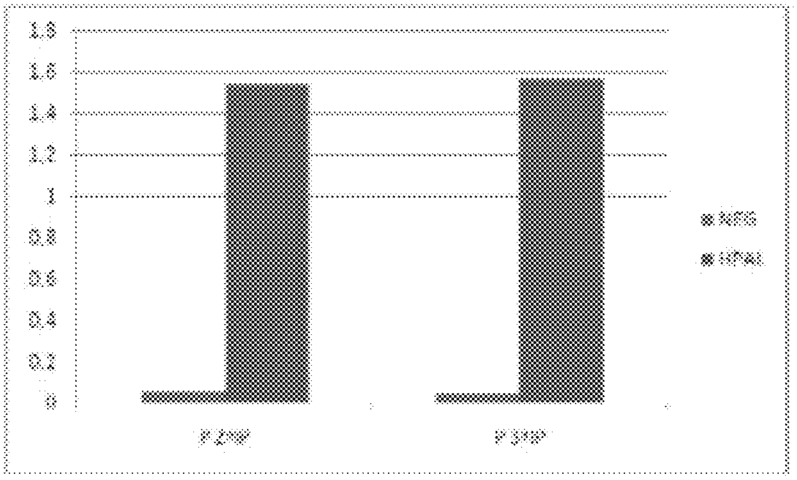
FIG. 11—Results of the demonstrations performed with the constructs containing the fragment PAL. A—Optical densities of ELISAs performed with sera from mice inoculated with CD1 HPAL (group HPAL) and CD1 without any treatment (Group NEG). The values represent the average of optical densities of 3 CD1 used. The CD1 were inoculated periodically and we carried out to the collection of sera periodically, according to the protocol described in Table 2. B—Immunoblottings performed with a nitrocellulose membrane containing the recombinant antigen HPAL. HPAL-nitrocellulose membrane containing the antigen HPAL stained with Schwartz solution. PM—molecular weights. Sera from harvest post 4th IP of negative group (a, b and c), the group inoculated with HPAL (d, e and f), diluted to 1/4000, were incubated with a strip of NC containing the antigen HPAL ON at 4° C. As conjugate we used protein G-HRP diluted 1/1000 and we proceeded to revelation with 4-chloro-naphthol.

PAL protein: This protein was shown to be very immunogenic. After obtaining the construct pQEHPAL we proceeded to the production and analysis of their recombinant antigens. Demonstration of the production of immune response was performed by inoculating CD1 mice with 30 μg of antigen HPAL (Table 2). The evaluation of the presence of specific antibody response was performed by ELISA with plates containing the antigen HPAL (FIG. 11A). There is the appearance of Ig G anti-PAL from the 2nd inoculation onwards.

Figure 11B:
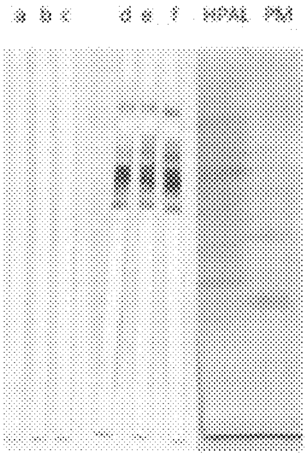

To assess the specificity of produced polyclonal antibodies we performed blots using as antigen the HPAL. There is, using the sera of harvest post 4th IP, diluted 1/4000, the appearance of precipitates corresponding to recombinant PAL (FIG. 11B) in the group HPAL.

Figure 12A:
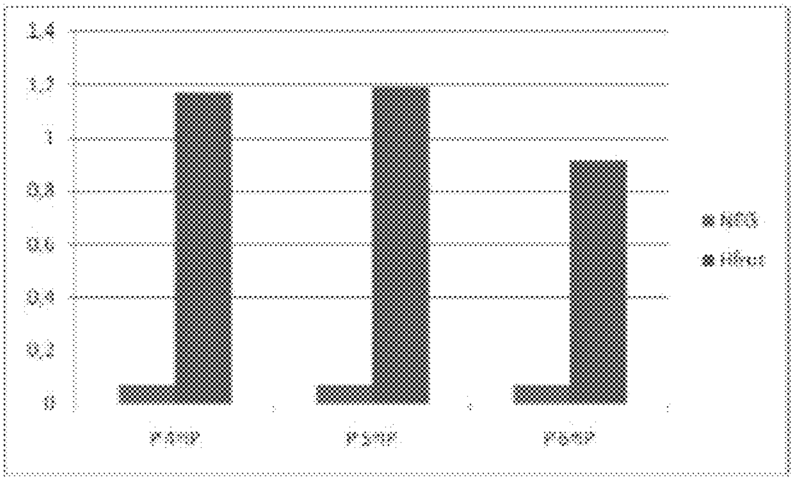
FIG. 12—Results of the demonstrations performed with the constructs containing the fragment LEC. A—Optical densities of ELISAs performed with sera from CD1 mice inoculated with HLEC (group HLEC) and CD1 without any treatment (Group NEG). The values represent the average of optical densities of 3 CD1 used. The CD1 were inoculated periodically and we carried out to the collection of sera periodically, according to the protocol described in Table 2. B—Immunoblottings performed with a nitrocellulose membrane containing the recombinant antigen HLEC. HLEC-containing nitrocellulose membrane antigen HLEC stained with Schwartz solution. PM—molecular weights. Sera from harvest post 6th IP of negative group (a, b and c) and the group inoculated with HLEC (d, e), diluted to 1/1000, were incubated with a strip of NC containing the antigen HLEC ON at 4° C. As conjugate we used protein G-HRP diluted 1/1000 and we proceeded to revelation with 4-chloro-naphthol.

LEC Protein: This protein was considered moderately immunogenic but due to its hemagglutinating activity, when in native form, we have developed specific antibodies against the antigen in denatured conditions. We proceeded to the production and analysis of recombinant antigen HLEC under denaturing conditions. Demonstration of the production of immune response was performed by inoculating CD1 mice with 12.5 μg of antigen HLEC. The evaluation of the presence of specific antibody response was performed by ELISA with plates containing the antigen HLEC (FIG. 12A). There is the appearance of IgG anti-LEC from the 4th inoculation onwards. The antibody levels reach a plateau after the 4th IP that was maintained during the period under review.

Figure 12B:
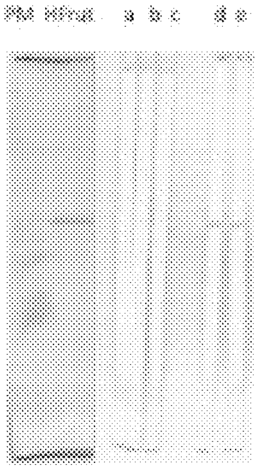

To assess the specificity of produced polyclonal antibodies we performed blots using as antigen the HLEC. There is, using sera harvested post 6th IP, diluted 1/1000, the appearance of precipitates corresponding to HLEC (FIG. 12 B) for the group HLEC.

The demonstrations described for the fragments CWG and CP12 showed that the presence of the fragment H in the recombinant protein can significantly increase the specific immune response developed by the mice. Thus the increase in immunogenicity is a characteristic associated with the recombinant antigen which allows the production of specific polyclonal antibodies, even though that in some of the extractions, including HEnt, HIL5, HPfsp HLEC the presence of *E. coli* contaminants was significant. So despite the contamination with proteins from *E. coli*, antibodies produced are essentially specific for the target fragment.

The development of polyclonal antibodies against a recombinant antigen may be associated with protection of host where they develop antibodies against the infectious organism that contains the corresponding antigen. This depends on a number of factors; especially the role or importance of this antigen has the mechanism of infection of infectious organism. In the case of mice inoculated with the protein HCP12, HCWG and HBG, these antigens represent, in the mechanism of infection by *Cryptosporidium* (CP12) and *Giardia* (CWG and BG), a crucial role in the invasion or cell adhesion to the host organism, and therefore, as described in the literature, are target candidates for vaccine development. The development of antibodies against these antigens has been described in the literature as protecting from infection by infectious agents (Tellez et al., 2003, Jenkins et al., 1998, Abdul-Wahid et al. 2007). In a very similar way to that described in previous literature, and to assess the protection of mice injected with HCP12, HCWG HBG in face of infection by the parasites *Cryptosporidium* and *Giardia*, we have indications that there is an effect of protection against infection by of mice pre-inoculated with these antigens.

The use of inocula consisting of soluble proteins eliminates much of the undesirable effects caused by adjuvants. In none of the mice used in described experiments were detected side effects that may result from inoculation of antigens. We also performed the production of polyclonal sera against some of the fragments described above (HCWG, HCP12, HToxo, HIL5, Hent and HBG) in the rabbit model using subcutaneous inoculations in the inner thigh and, as in mice, we didn't observe any side effects from the administration of antigens. As in model mice, rabbits produced evidence of very significant polyclonal antibodies against the antigen of interest. In all targets evaluated we could demonstrate the existence of a significant immune response by demonstrating the production of specific Ig.

Another very important feature, observed particularly in the case of the response against HCWG, HCD4, HPfsp, Hent and HBG, is that it was possible to detect specific response up to 3 months after last immunization, suggesting the development of memory cells, a characteristic essential for the development of vaccines.

Although the examples given are based on models for production of recombinant proteins that produce antigen fusion containing the fragment H, this fragment can be added to the targets through other processes. The activity shown should be included in the field of adjuvants and as they can be used in various formulations in order to improve or increase the intensity and specificity of the immune response resulting from the application of a target antigen.

The invention claimed is:

1. An immunogen, comprising:

a fusion protein that includes:

(a) an adjuvant N-terminal fragment of FH8 from *Fasciola hepatica*, said fragment including the amino acid sequence set out in SEQ ID NO 2; and (b) an antigenic protein or antigenic protein fragment, wherein the antigenic protein or antigenic protein fragment is from a pathogenic protein other than FH8.

2. The immunogen according to claim 1, wherein the antigenic protein or antigenic protein fragment is derived from at least one of *Giardia lamblia* cysts (CWG), *Dicentrarchus labrax* (CD4), human interleukin 5 (IL5), *Plasmodium falciparum* (Pfsp), *Entamoeba histolytica* (Ent), *Legionella pneumophilia* (PAL), *Cryptosporidium parvum* (CP12), *Artocarpus incisa* (LEC), *Giardia lamblia* (BG) or *Toxoplasma gondii* (Toxo).

3. A composition, comprising: the immunogen of claim 1.

4. The composition according to claim 3, further comprising the immunogen in a therapeutically effective amount and a pharmacologically suitable vehicle.

5. The composition according to claim 3, wherein the composition includes no more than one immunogen described in claim 1.

6. The composition according to claim 3, further comprising an immunogen with a concentration at 1 to 100 μg in a volume between 100 and 1000 μl diluted in phosphate buffer comprising 0.01 M phosphate, 0.1 M NaCl, pH 7.2.

7. The composition of claim 3, wherein the composition is a medicine.

8. An adjuvant, comprising: the immunogen of claim 1 or a pharmaceutical composition thereof.

9. A vaccine, comprising: the immunogen of claim 1 or a pharmaceutical composition thereof.

10. A method for the preparation of the immunogen of claim 1, the method comprising: fusing the N-terminal fragment of FH8 from *Fasciola hepatica*, said fragment including the amino acid sequence set out in SEQ ID NO 2, to an antigenic protein or an antigenic protein fragment.

11. The method according to claim 10, wherein the antigenic protein or antigenic protein fragment is derived from at least one of *Giardia lamblia* cysts (CWG), *Dicentrarchus labrax* (CD4), human interleukin 5 (IL5), *Plasmodium falciparum* (Pfsp), *Entamoeba histolytica* (Ent), *Legionella pneumophilia* (PAL), *Cryptosporidium parvum* (CP12), *Artocarpus incisa* (LEC), *Giardia lamblia* (BG) or *Toxoplasma gondii* (Toxo).

12. A method for production of polyclonal antibodies capable of recognizing the immunogen described in claim 1, comprising:

(a) immunizing a non-human mammal subject with the immunogen of claim 1; and (b) selecting antibodies that are able to recognize the immunogen.

13. A method for the preparation of the immunogen of claim 1, comprising: fusing the N-terminal fragment of FH8 from *Fasciola hepatica*, said fragment including the amino acid sequence set out in SEQ ID NO 2, to an antigenic protein or an antigenic protein fragment.

14. A method for the preparation of the immunogen of claim 2, comprising: fusing the N-terminal fragment of FH8 from *Fasciola hepatica*, said fragment including the amino acid sequence set out in SEQ ID NO 2, to an antigenic protein or an antigenic protein fragment.

* * * * *

SEQUENCE LISTING

```
<160> NUMBER OF SEQ ID NOS: 12

<210> SEQ ID NO 1
<211> LENGTH: 69
<212> TYPE: PRT
<213> ORGANISM: Fasciola hepatica

<400> SEQUENCE: 1

Met Pro Ser Val Gln Glu Val Glu Lys Leu Leu His Val Leu Asp Arg
1               5                   10                  15

Asn Gly Asp Gly Lys Val Ser Ala Glu Glu Leu Lys Ala Phe Ala Asp
            20                  25                  30

Asp Ser Lys Cys Pro Leu Asp Ser Asn Lys Ile Lys Ala Phe Ile Lys
        35                  40                  45

Glu His Asp Lys Asn Lys Asp Gly Lys Leu Asp Leu Lys Glu Leu Val
    50                  55                  60

Ser Ile Leu Ser Ser
65


<210> SEQ ID NO 2
<211> LENGTH: 11
<212> TYPE: PRT
<213> ORGANISM: Fasciola hepatica

<400> SEQUENCE: 2

Met Pro Ser Val Gln Glu Val Glu Lys Leu Leu
1               5                   10


<210> SEQ ID NO 3
<211> LENGTH: 133
<212> TYPE: PRT
<213> ORGANISM: Fasciola hepatica

<400> SEQUENCE: 3

Pro Tyr Met Met Glu Ile His Val Gln Cys Asn Thr Asp Leu Val Cys
1               5                   10                  15

Thr Ala Ala Pro Asp Thr Tyr Thr Gly Ile Tyr Leu Cys Gly Thr Thr
            20                  25                  30

Asp Cys Asp Tyr Cys Thr Ala Leu Pro Pro Thr Asn Cys Pro Thr Thr
        35                  40                  45
```

-continued

```
Leu Glu Arg Asp Gly Cys Thr Tyr Tyr Arg Gln Thr Val Val Arg Asn
    50                  55                  60

Ala Ser Gly Arg Lys Thr Ser Cys Asn Ala Arg Ser Ala Ser Asn Cys
65                  70                  75                  80

Gly Lys Ala Lys Ser Asn Met His Asn Ser Ala His Asn Ala Gln Arg
                85                  90                  95

Lys Cys Asn Met Pro Asn Ser Arg Ser Gln Thr Pro Leu Arg Thr Val
            100                 105                 110

Val Arg Ser Ser Ser Lys Thr Ala Ser Thr Ser Arg Ser Arg Thr Ala
        115                 120                 125

Pro Lys Lys Thr Val
    130


<210> SEQ ID NO 4
<211> LENGTH: 178
<212> TYPE: PRT
<213> ORGANISM: Fasciola hepatica

<400> SEQUENCE: 4

Glu Leu Glu Glu Leu Ile Tyr Ala Glu Glu Gly Gln Met Val Thr Leu
1               5                   10                  15

Asn Pro Pro Ala Val Thr Asn Pro Gln Thr His Tyr Ser Tyr Trp Val
            20                  25                  30

Phe Asn Gly Asn Gln Ile Ala Trp Arg Asn Pro Phe Ser Gly Lys Gly
        35                  40                  45

Val Asn Asp Lys Asp Ser Leu Ser Leu Thr Asp Gly Ser Val Leu Val
    50                  55                  60

Ile Thr Asn Ile Gln Gln Asn Leu Phe Gly Thr Phe Thr Cys Gln Ile
65                  70                  75                  80

Tyr Thr Ser Gly Asn Arg Asp Thr Pro Val Asp Thr Thr Thr Tyr Lys
                85                  90                  95

Ile Leu Lys Leu Ser Val Thr Met Asp Pro Pro Ser Pro Leu Leu Pro
            100                 105                 110

Gly Glu Asp Leu Ser Leu Asn Cys Asn Ala Gly Arg Asn Pro Lys Ile
        115                 120                 125

His Trp Leu Asp Pro Gln Gly Gln Lys Ile Asn Ser Gln Arg Ile Gln
    130                 135                 140

Gln Lys Ala Thr Gly Gln Asp Lys Gly Glu Trp Thr Cys Val Val Thr
145                 150                 155                 160

Tyr Ser Asn Lys Glu Ser Lys Ala Lys Ile Ser Val Thr Leu Val Asp
                165                 170                 175

Gly Thr


<210> SEQ ID NO 5
<211> LENGTH: 48
<212> TYPE: PRT
<213> ORGANISM: Fasciola hepatica

<400> SEQUENCE: 5

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45
```

-continued

<210> SEQ ID NO 6
<211> LENGTH: 55
<212> TYPE: PRT
<213> ORGANISM: Fasciola hepatica

<400> SEQUENCE: 6

```
Glu Gly Val Tyr Asn Gly Thr Cys Ser Glu Glu Leu Asn His Ser Val
1               5                   10                  15

Leu Leu Val Gly Tyr Gly Gln Val Glu Lys Thr Lys Leu Asn Tyr Asn
            20                  25                  30

Asn Lys Ile Gln Thr Tyr Asn Thr Lys Glu Asn Ser Asn Gln Pro Asp
        35                  40                  45

Asp Asn Ile Ile Tyr Tyr Trp
    50                  55
```

<210> SEQ ID NO 7
<211> LENGTH: 43
<212> TYPE: PRT
<213> ORGANISM: Fasciola hepatica

<400> SEQUENCE: 7

```
Glu Val Lys Glu Gly Tyr Tyr Cys Tyr Glu Glu Glu Ser Lys Asn Thr
1               5                   10                  15

Glu Tyr Tyr Trp Cys Val Asn Asn Val Gly Tyr Glu Met Lys Cys Pro
            20                  25                  30

Asn Gly Thr Thr Cys His Thr Lys Asp Ile Gly
        35                  40
```

<210> SEQ ID NO 8
<211> LENGTH: 176
<212> TYPE: PRT
<213> ORGANISM: Fasciola hepatica

<400> SEQUENCE: 8

```
Met Lys Ala Gly Ser Phe Tyr Lys Leu Gly Leu Leu Val Ala Ser Ala
1               5                   10                  15

Val Leu Val Ala Ala Cys Ser Lys Thr Pro Gly Ser Ala Asp Gly Gly
            20                  25                  30

Ala Ala Val Gly Asp Gly Asp Ala Thr Ala Gln Gly Leu Gly Gln Met
        35                  40                  45

Thr His Phe Ala Gly Gln Glu Pro Gly Glu Ser Tyr Thr Thr Gln Ala
    50                  55                  60

Pro His Asn Gln Leu Tyr Leu Phe Ala Tyr Asp Asp Ser Thr Leu Ala
65                  70                  75                  80

Ser Lys Tyr Leu Pro Ser Val Asn Ala Gln Ala Glu Tyr Leu Lys Thr
                85                  90                  95

His Pro Gly Ala Arg Val Met Ile Ala Gly His Thr Asp Glu Arg Gly
            100                 105                 110

Ser Arg Glu Tyr Asn Val Ala Leu Gly Glu Arg Arg Ala Asp Thr Val
        115                 120                 125

Ala Glu Ile Leu Arg Met Ala Gly Val Ser Arg Gln Gln Ile Arg Val
    130                 135                 140

Val Ser Tyr Gly Lys Glu Arg Pro Ala Asn Tyr Gly His Asp Glu Ala
145                 150                 155                 160

Ser His Ala Gln Asn Arg Arg Val Glu Phe Ile Tyr Glu Ala Thr Arg
                165                 170                 175
```

<210> SEQ ID NO 9

<211> LENGTH: 73
<212> TYPE: PRT
<213> ORGANISM: Fasciola hepatica

<400> SEQUENCE: 9

Glu Leu Glu Gly Val Leu Trp His Asn Val Phe Glu Gln Asp Arg Leu
1 5 10 15

Gln Trp Gln Pro Glu Arg Asn Asp Ala Gln Asn Phe Thr Asn Gly Asn
20 25 30

Gln Tyr Asn Tyr Ile Gln Val Pro Thr Asp Phe Asn Ser Val Met Gly
35 40 45

Gly Leu Gln Ser Pro Ser Glu Met Ala Arg Thr Ile Glu Arg Asn Ile
50 55 60

Glu Lys Lys Gln Met Asn Glu Gln Ile
65 70

<210> SEQ ID NO 10
<211> LENGTH: 176
<212> TYPE: PRT
<213> ORGANISM: Fasciola hepatica

<400> SEQUENCE: 10

Met Pro Ser Val Gln Glu Val Glu Lys Leu Leu Glu Leu Asp Asp Asp
1 5 10 15

Asp Lys Met Ala Glu Gln Ser Gly Lys Ser Gln Thr Val Ile Val Gly
20 25 30

Pro Trp Gly Ala Lys Val Ser Thr Ser Ser Asn Gly Lys Ala Phe Asp
35 40 45

Asp Gly Ala Phe Thr Gly Ile Arg Glu Ile Asn Leu Ser Tyr Asn Lys
50 55 60

Glu Thr Ala Ile Gly Asp Phe Gln Val Ile Tyr Asp Leu Asn Gly Arg
65 70 75 80

Pro Phe Val Gly Gln Ser His Thr Ser Phe Ile Lys Gly Phe Thr Pro
85 90 95

Val Lys Ile Ser Leu Asp Phe Pro Ser Glu Tyr Ile Val Glu Val Ser
100 105 110

Gly His Thr Gly Lys Val Ser Gly Tyr Val Val Val Arg Ser Leu Thr
115 120 125

Phe Lys Thr Asn Lys Lys Thr Tyr Gly Pro Tyr Gly Val Thr Ser Gly
130 135 140

Thr Pro Phe Asn Leu Pro Ile Glu Asn Gly Leu Val Val Gly Phe Lys
145 150 155 160

Gly Ser Ile Gly Tyr Trp Met Asp Tyr Phe Ser Met Tyr Leu Ser Leu
165 170 175

<210> SEQ ID NO 11
<211> LENGTH: 273
<212> TYPE: PRT
<213> ORGANISM: Fasciola hepatica

<400> SEQUENCE: 11

Met Ser Met Phe Thr Ser Thr Arg Thr Leu Thr Gln Thr Met Asp Lys
1 5 10 15

Pro Asp Asp Leu Thr Arg Ser Ala Thr Glu Thr Ala Val Lys Leu Ser
20 25 30

Asn Met Asn Gln Arg Val Ser Arg Phe His Asp Lys Met Glu Asn Glu
35 40 45

-continued

```
Ile Glu Val Arg Arg Val Asp Asp Asp Thr Arg Val Val Lys Met Ile
    50                  55                  60

Lys Asp Ala Ile Ala His Leu Asp Arg Leu Ile Gln Thr Glu Ser Arg
65                  70                  75                  80

Lys Arg Gln Ala Ser Phe Glu Asp Ile Arg Glu Glu Val Lys Lys Ser
                85                  90                  95

Ala Asp Asn Met Tyr Leu Thr Ile Lys Glu Glu Ile Asp Thr Met Ala
            100                 105                 110

Ala Asn Phe Arg Lys Ser Leu Ala Glu Met Gly Asp Thr Leu Asn Asn
        115                 120                 125

Val Glu Thr Asn Leu Gln Asn Gln Ile Ala Ile His Asn Asp Ala Ile
    130                 135                 140

Ala Ala Leu Arg Lys Glu Ala Leu Lys Ser Leu Asn Asp Leu Glu Thr
145                 150                 155                 160

Gly Ile Ala Thr Glu Asn Ala Glu Arg Lys Lys Met Tyr Asp Gln Leu
                165                 170                 175

Asn Glu Lys Val Ala Glu Gly Phe Ala Arg Ile Ser Ala Ala Ile Glu
            180                 185                 190

Lys Glu Thr Ile Ala Arg Glu Arg Ala Val Ser Ala Ala Thr Thr Glu
        195                 200                 205

Ala Leu Thr Asn Thr Lys Leu Val Glu Lys Cys Val Asn Glu Gln Leu
    210                 215                 220

Glu Asn Val Ala Ser Glu Ile Arg Ala Ile Gln Glu Glu Ile Asp Arg
225                 230                 235                 240

Glu Lys Ala Glu Arg Lys Glu Ala Glu Asp Lys Ile Val Asn Thr Leu
                245                 250                 255

Glu Asp Val Val Ser Lys Ile Gln Gly Gly Leu Ser Met Val Thr Lys
            260                 265                 270

His


<210> SEQ ID NO 12
<211> LENGTH: 120
<212> TYPE: PRT
<213> ORGANISM: Fasciola hepatica

<400> SEQUENCE: 12

Pro Pro Val Pro Ser Cys Pro Pro Gly Phe Ser Leu Glu Gln Arg Gly
1               5                   10                  15

Cys Val Arg Ser Arg Gln Val Pro Pro Ile Met Arg Cys Ala Lys Lys
            20                  25                  30

Ser Val Leu Ala Gly Asn Glu Cys Val Thr Thr Glu Phe Ala Pro Ser
        35                  40                  45

Ile Glu Val Cys Pro Glu Gly Phe Ile Glu Lys Asn Arg Lys Cys Arg
    50                  55                  60

Arg Val Val Asn Ala Gln Pro Gln Leu Gly Cys Lys Pro Gly Phe Thr
65                  70                  75                  80

Leu Gln Asn Gly Gly Asp Cys Ile Arg Val Thr Glu Asp Asp Ile Ile
                85                  90                  95

Thr Arg Cys Pro Pro Lys Ser Lys His Thr Ser Lys Gly Cys Val Thr
            100                 105                 110

Val Glu Lys Leu Asp Val Val Pro
        115                 120
```